US006787126B1

(12) United States Patent
Heneine et al.

(10) Patent No.: US 6,787,126 B1
(45) Date of Patent: Sep. 7, 2004

(54) METHOD AND KIT FOR DETECTING RESISTANCE TO ANTIVIRAL DRUGS

(75) Inventors: Walid M. Heneine, Atlanta, GA (US); Gerardo Garcia Lerma, Atlanta, GA (US); Shinji Yamamoto, Kumamoto (JP); William M. Switzer, Stone Mountain, GA (US); Thomas M. Folks, Snellville, GA (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/719,906

(22) PCT Filed: Jun. 18, 1999

(86) PCT No.: PCT/US99/13957

§ 371 (c)(1),
(2), (4) Date: Jul. 30, 2001

(87) PCT Pub. No.: WO99/66068

PCT Pub. Date: Dec. 23, 1999

Related U.S. Application Data

(60) Provisional application No. 60/090,051, filed on Jun. 19, 1998.

(51) Int. Cl.$^7$ .............................. C12Q 1/00; C12Q 1/70
(52) U.S. Cl. ................................ 424/9.1; 435/4; 435/5; 435/32
(58) Field of Search ................ 435/4, 5, 32; 536/24.33; 424/9.1

(56) References Cited

U.S. PATENT DOCUMENTS

| | | |
|---|---|---|
| 5,631,128 A | 5/1997 | Kozal et al. |
| 5,849,494 A | 12/1998 | Heneine et al. |
| 6,136,934 A | 10/2000 | Reuven et al. |

FOREIGN PATENT DOCUMENTS

| | | |
|---|---|---|
| WO | WO 93 23574 | 11/1993 |
| WO | WO 96 23076 | 8/1996 |
| WO | WO 97 27319 | 7/1997 |

OTHER PUBLICATIONS

Arts and Wainberg, "Mechanisms of Nucleoside Analog Antiviral Activity and Resistance during Human Immunodeficiency Virus Reverse Transcription," *Antimicrob. Agents Chemother.* 40(3) : 527–540 (Mar. 1996).

Carroll et al., "Sensitivity of HIV–1 Reverse Transcriptase and Its Mutants to Inhibition by Azidothymidine Triphosphate," *Biochemistry* 33:2113–2120 (1994).

Garcia–Lerma et al., "Measurement of Human Immunodeficiency Virus Type 1 Plasma Virus Load Based on Reverse Transcriptase (RT) Activity: Evidence of Variabilities in Levels of Virion–Associated RT," *J. Infect. Dis.* 177:1221–1229 (1998).

Kavlick et al., "Emergence of Multi–Dideoxynucleoside–Resistant Human Immunodeficiency Virus Type 1 Variants, Viral Sequence Variation, and Disease Progression in Patients Receiving Antiretroviral Chemotherapy," *J. Infect. Dis.* 98:1506–1513 (Jun. 1998).

Kerr et al., "Pre–Steady–State Kinetic Characterization of Wild Type and 3'–Azido–3'–deoxythymidine (AZT) Resistant Human Immunodeficiency Virus Type 1 Reverse Transcriptase: Implication of RNA Directed DNA Polymerization in the Mechanism of AZT Resistance," *Biochemistry* 36:14064–14070 (1997).

Krebs et al., "Single–Step Kinetics of HIV–1 Reverse Transcriptase Mutants Responsible for Virus Resistance to Nucleoside Inhibitors Zidovudine and 3–TC," *Biochemistry* 36:10292–10300 (1997).

Lacey et al., "Biochemical Studies on the Reverse Transcriptase and RNase H Activities from Human Immunodeficiency Virus Strains Resistant to 3'–Azido–3'–deoxythymidine," *J. Biol. Chem.* 267 (22): 15789–15794 (Aug. 1992).

Larder et al., "HIV with Reduced Sensitivity to Zidovudine (AZT) Isolated During Prolonged Therapy," *Science* 243: 1731–1734 (Mar. 1989).

Maeda et al., "Altered Drug Sensitivity, Fitness, and Evolution of Human Immunodeficiency Virus Type 1 with pol Gene Mutations Conferring Multi–Dideoxynucleoside Resistance," *J. Infect. Dis.* 177: 1207–1213 (May 1998).

Mellors et al., "Mutations in HIV–1 Reverse Transcriptase and Protease Associated with Drug Resistance," *International Antiviral News* 3(1):8–13 (Jan. 1995).

Nguyen et al., "Resistance of Human Immunodeficiency Virus Type 1 to Acyclic 6–Phenylselenenyl–and 6–Phenylthiopyrimidines," *Antimicrobial Agents and Chemotherapy* 38(10):2409–2414 (Oct. 1994).

Schmit et al., "Multiple Drug Resistance to Nucleoside Analogues and Nonnucleoside Reverse Transcriptase Inhibitors in an Efficiently Replicating Human Immunodeficiency Virus Type 1 Patient Strain," *J. Infect. Dis.* 174: 962–968 (1996).

(List continued on next page.)

*Primary Examiner*—Stacy B. Chen
(74) *Attorney, Agent, or Firm*—Needle & Rosenberg, P.C.

(57) ABSTRACT

An assay and kit for the detection of phenotypic resistance of a retrovirus to a reverse transcriptase inhibitor drug in a biological sample. The assay is based on the direct analysis of the susceptibility of retroviral reverse transcriptase to inhibition by a reverse transcriptase inhibitor drug. The enzymatic activity of the reverse transcriptase is determined by measuring the DNA product produced when an RNA template and a first complementary DNA primer from a suitable region of the encephalomyocarditis virus genome are incubated with a biological sample containing reverse transcriptase in the presence of the drug to which resistance is being determined.

8 Claims, 7 Drawing Sheets

Shafer et al., "Drug Resistance and Heterogeneous Long-Term Virologic Responses of Human Immunodeficiency Virus Type 1–Infected Subjects to Zidovudine and Didanosine Combination Therapy," *J. Infect. Dis.* 172:70–78 (Jul. 1995).

Shirasaka et al., "Changes in drug sensitivity of human immunodeficiency virus type 1 during therapy with azidothymidine, dideoxycytidine, and dideoxyinosine: An in vitro comparative study," *Proc. Nat. Acad. Sci. USA* 90: 562–566 (1993).

Ueno et al., "Comparative Enzymatic Study of HIV–1 Reverse Transcriptase Resistant to 2', 3'–Dideoxynucleotide Analogs Using the Single–Nucleotide Incorporation Assay," *Biochemistry* 36: 1092–1099 (1997).

Ueno et al., "Enzymatic Characterization of Human Immunodeficiency Virus Type 1 Reverse Transcriptase Resistant to Multiple 2',3'–Dideoxynucleoside 5'–Triphosphates," *J. Biol. Chem.* 270 (40) : 23605–23611 (Oct. 1995).

Yamamoto et al., "Highly sensitive qualitative and quantitative detection of reverse transcriptase activity: optimization, validation, and comparative analysis with other detection systems," *J. Virol. Methods* 61: 135–143 (1996).

Petropoulos et al. "A Novel Phenotypic Drug Susceptibility Assay for Human Immunodeficiency Virus Type 1" *Antimicrobial Agents and Chemotherapy* 44(4):920–928, Apr. 2000.

Garcia Lerma et al. "A Rapid Non–Culture–Based Assay for Clinical Monitoring of Phenotypic Resistance of Human Immunodeficiency Virus Type 1 to Lamivudine (3TC)" *Antimicrobial Agents and Chemotherapy* 43 (2) :264–270, Feb. 1999.

Hertogs et al., "A Rapid Method for Simultaneous Detection of Phenotypic Resistance to Inhibitors of Protease and Reverse Transcriptase in Recombinant Human Immunodeficiency Virus Type 1 Isolates from Patients Treated with Antiretroviral Drugs" *Antimicrobial Agents and Chemotherapy* 42(2):269–276, Feb. 1998.

Stuyver et al. "Line Probe Assay for Rapid Detection of Drug–Selected Mutations in the Human Immunodeficiency Virus Type 1 Reverse Transcriptase Gene" *Antimicrobial Agents and Chemotherapy* 41(2):284–291, Feb. 1997.

Gulick et al. "Treatment with Indinavir, Zidovudine, and Lamivudine in Adults with Human Immunodeficiency Virus Infection and Prior Antiretroviral Therapy" *N. Engl. J. Med.* 337(11):734–739 (1997).

Havlir et al. "Nevirapine–Resistant Human Immunodeficiency Virus: Kinetics of Replication and Estimated Prevalence in Untreated Patients" J. Virol. 70(11):7894–7899 (Nov. 1996).

Schinazi et al. "Mutations in retroviral genes associated with drug resistance" *International Antiviral News* 4(6):95–107, 1996.

Kavlick et al. "Genotypic and phenotypic characterization of HIV–1 isolated from patients receiving (–) –2', 3'–dideoxy–3'–thiacytidine" *Antiviral Research* 28:133–146 (1995).

Wainberg et al. "Development of HIV–1 resistance to (–)2'–deoxy–3'–thiacytidine in patients with AIDS or advanced AIDS–related complex" *AIDS* 9:351–357 (1995).

Frenkel et al. Specific, Sensitive, and Rapaid Assay for Human Immunodeficiency Virus Type 1 pol Mutations Associated with Resistance to Zidovudine and Didanosine *J. Clin. Microbiol.* 33 (2) :342–347 (Feb. 1995).

Larder et al. "Potential Mechanism for Sustained Antiretroviral Efficacy of AZT–3TC Combination Therapy" *Science* 269:696–699 (Aug. 1995).

Heneine et al. "Detection of Reverse Transcriptase by a Highly Sensitive Assay in Sera from Persons Infected with Human Immunodeficiency Virus Type 1" *J. Infect. Diseases* 171:1210–1216 (1995).

Shirasaka et al. "Emergence of human immunodeficiency virus type 1 variants with resistance to multiple dideoxynucleosides in patients receiving therapy with dideoxynucleosides" *Proc. Natl. Acad. Sci. USA* 92:2398–2402 (Mar. 1995).

Mulder et al. "Rapid and Simple PCR Assay for Quantitation of Human Immunodeficiency Virus Type 1 RNA in Plasma: Application to Acute Retroviral Infection" *J. Clin. Microbiol.* 32(2) :292–300 (Feb. 1994).

Schinazi et al. "Selective Inhibition of Human Immunodeficiency Viruses by Racemates and Enantiomers of cis–5–Fluoro–1–[2 –(Hydroxymethyl)–1, 3–Oxathiolan–5–yl] Cytosine" *Antimicrobial Agents and Chemotherapy* 36(11) :2423–2431 (Nov. 1992).

Li et al. "Molecular Characterization of Human Immunodeficiency Virus Type 1 Cloned Directly from Uncultured Human Brain Tissue: Identification of Replication–Competent and Defective Viral Genomes" *J. Virol.* 65(8):3973–3985 (Aug. 1991).

Richman et al. "Human immunodeficiency virus type 1 mutants resistant to Nonnucleoside inhibitors of reverse transcriptase arise in tissue culture" *Proc. Natl. Acad. Sci. USA* 88:11241–11245 (Dec. 1991).

Larder et al. "Multiple Mutationsin HIV–1 Reverse Transcriptase Confer High–Level Resistance to Zidovudine (AZT)" *Science* 246:1155–1158 (1989).

METHOD AND KIT FOR DETECTING RESISTANCE TO ANTIVIRAL DRUGS

The present application is a 35 U.S.C. § 371 national phase application from, and claims priority to, international application PCT/US99/13957, filed Jun. 18, 1999 (published under PCT Article 21(2) in English), which claims priority to U.S. provisional patent application Serial No. 60/090,051, filed Jun. 19, 1998, which applications are incorporated herein in their entirety by reference.

This invention was made by the Centers for Disease Control and Prevention, an agency of the United States Government.

TECHNICAL FIELD

The present invention relates in general to assays for detecting resistance of a retrovirus to reverse transcriptase inhibitor therapies and more specifically relates to a non-culture, polymerase chain reaction-based phenotypic assay for detecting antiviral drug-resistant reverse transcriptase activity in a sample from a patient infected with a retrovirus.

BACKGROUND OF THE INVENTION

One of the most ravaging diseases of the late twentieth century has been AIDS (acquired immunodeficiency syndrome), brought on by HIV (human immunodeficiency virus) infection. Currently, there are no cures for this disease and minimally effective treatments. One of the problems that exists in the development of therapies for HIV infection is that the HIV virus rapidly develops resistance to a wide variety of chemotherapeutic agents. HIV, particularly human immunodeficiency virus type 1 (HIV-1), mutates over time to become resistant to many of the antiviral drugs administered for treatment. AIDS physicians need to know when the antiviral therapy being used to treat a individual patient is no longer effective so that the antiviral drug or drug combination can be modified, thereby minimizing viral replication and the onset of immunodeficiency symptoms.

Reverse transcriptase (RT) inhibitors such as zidovudine (ZDV, also referred to as azidothyimidine (AZT)), didanosine (ddI or dideoxyinosine), zalcitabine (ddC or dideoxycytosine), lamivudine (3TC), stavudine (d4T), and nevirapine (NVP) are nucleoside or non-nucleoside analogs currently approved for the treatment of HIV-1 infections. 3TC is known to have potent anti-HIV-1 activity and minimal toxicity, and is one of the most commonly used drugs in combination therapy as first-line treatment for HIV-1-infected patients. 3TC administered in combination with AZT provides greater and more sustained increases in CD4+ cell counts, and higher reductions in HIV-1 RNA viral load than continued AZT or 3TC monotherapy. 3TC in combination with AZT and protease inhibitors slows the progression of HIV-1 disease and reduces levels of HIV-1 RNA to less than 500 copies per milliliter for as long as one year in 90% of patients (Gulick et al., *N. Engl. J. Med.* 1997;337:734–739).

However, the use of reverse transcriptase inhibitors, such as 3TC, in both monotherapy or combination therapy has resulted in the emergence of drug-resistant variants of HIV-1 (Gulick et al., 1997). For a drug such as 3TC, the resistance is conferred by mutations in codon 184 of the HIV-1 reverse transcriptase gene, which replaces the wild type methionine residue (M; ATG) with a valine (V; GTG) via a transient substitution with an isoleucine (I; ATA). The presence of this M184V mutation has been associated with a greater than 500-fold resistance to 3TC and the partial loss of the anti-retroviral and clinical benefits of the drug. It is therefore important to monitor for drug resistance in individuals treated with reverse transcriptase inhibitors.

Phenotypic assays provide direct and definitive evidence of resistance to reverse transcriptase inhibitor drugs. However, presently available assays for the analysis of phenotypic resistance are based on virus culture and are therefore labor intensive and time consuming (two to five weeks), costly, and unsuitable for rapid clinical monitoring or surveillance of drug resistance (Kavlick et al., *Antiviral Research* 1995;28:133–146; Wainberg et al., *AIDS* 1995;9:351–357). In addition, these assays are fraught with biologic variabilities, including those related to viral isolation and tropism. Since tissue culture is highly selective for viral strains with in vitro growth advantages, these culture-based assay methods may not be representative of the total virus population present in vivo (Li et al., *J. Virol.* 1991;65:3973–3985].

In the absence of rapid phenotypic assays, genotypic tests are currently being used to provide indirect evidence of resistance. Genotypic testing monitors for the presence of mutations that are associated with resistance, such as the M184V mutation. Among these genotypic tests, primer-specific PCR, point mutation, and reverse hybridization assays are the most commonly used (Wainberg et al., 1995; Frenkel et al.,*J. Clin. Microbiol.* 1995;33:342–347; Stuyver et al., *Antimicrob. Agents Chemother.* 1997;41:284–291). Unfortunately, clinical monitoring of reverse transcriptase inhibitor drug resistance by genotypic testing may not detect unrecognized mutations or potential synergistic or antagonistic effects of complex mutation patterns arising from combination therapy with different reverse transcriptase inhibitors. For example, the suppression of phenotypic resistance to AZT conferred by the M184V mutation clearly illustrates the effect that a combination of mutations may have in a given phenotype (Larder et al., *Science* 1995;269:696–699). Also, genotypic testing only detects resistance associated with known mutations (i.e., codon 184 for 3TC resistance).

U.S. Pat. No. 5,631,128 to Kozal describes polymerase chain reaction (PCR) assays for monitoring antiviral therapies in the treatment of AIDS. These genotypic assays use PCR to measure HIV-1 RNA copy number in plasma or to measure specific known HIV-1 RNA mutations, namely the mutation at codon 215 or codon 74 of the pol gene. The HIV-1 DNA copy number is an indication of the circulating HIV viral load. A decrease in HIV-1 RNA copy number correlates with successful antiretroviral therapy, whereas an increase in HIV-1 RNA copy number indicates disease progression, most likely caused by resistance to therapy. Therefore, the genotypic assays described in U.S. Pat. No. 5,631,128 detect only previously identified viral RNA mutations and are incapable of detecting phenotypic resistance caused by known or novel mutations, or the assays detect a rise in HIV-1 RNA copy number, which could be due to conditions other than resistance. An incorrect diagnosis of drug resistance followed by cessation of the antiviral therapy being administered could result in exacerbation of a disease that had been responding to therapy.

Therefore, there is a need for sensitive, rapid methods for the detection of HIV resistance to drug therapies in patients so that, if the virus becomes resistant to a particular drug or combination of drugs, the therapy can be modified, thereby keeping viral replication to a minimum and preventing or postponing the onset of AIDS.

SUMMARY OF THE INVENTION

An assay and kit for the detection of phenotypic resistance to a reverse transcriptase inhibitor drug in a biological sample is provided. Preferably, the biological sample is from a patient infected with a retrovirus. The assay is based on the direct analysis of the susceptibility of retroviral reverse transcriptase to inhibition by a reverse transcriptase inhibitor drug.

The enzymatic activity of the reverse transcriptase enzyme is determined by measuring the DNA product produced when an RNA template and a first complementary DNA primer from a suitable region of the encephalomyocarditis virus genome are incubated with a biological sample containing reverse transcriptase in the presence of the drug to which resistance is being determined. As a control, the enzymatic activity of the reverse transcriptase enzyme is also determined in the absence of the drug. The incubation mixture is reacted under conditions whereby the RNA template and the DNA primer will anneal and a DNA strand will be synthesized as an extension from the DNA primer if the reverse transcriptase in the sample is resistant to and not inhibited by the drug. The DNA product is amplified using a second complementary DNA primer from the encephalomyocarditis virus genome and suitable PCR reagents and conditions, and the amplified product detected in accordance with methods known to those skilled in the art. Detection of the amplified DNA indicates resistance to the drug employed in the assay. The difference in reverse transcriptase activity in the assays with and without drug verifies a finding of resistance and provides an indication as to the degree of resistance to the drug.

Preferably, the biological sample under investigation is a biological fluid, most preferably 0.5 $\mu$l to 1.0 ml of blood plasma or serum Preferably, the RNA template consists of the ribonucleotide of SEQ ID NO:4; the first DNA primer consists of the oligonucleotide of SEQ ID NO:2; the second DNA primer consists of the oligonucleotide of SEQ ID NO:1; and PCR amplification is achieved by utilizing 30–40 cycles of heating the synthesized DNA and primer pair to 93 to 97° C. for 30 to 90 seconds, at 53 to 57° C. for 30 to 90 seconds, and at 70 to 74° C. for 30 to 90 seconds. The amplified synthesized DNA is preferably detected by hybridization to an internal specific oligoprobe using an enzyme linked immunosorbent assay (ELISA), Southern blot hybridization methods, or similar methods.

Additionally provided is a kit for determining reverse transcriptase inhibitor drug resistance in a biological sample. The kit contains a suitable region of the encephalomyocarditis virus genome as an RNA template, a first complementary DNA primer for reverse transcriptase, and a second complementary DNA primer for amplification via the polymerase chain reaction, and the RT inhibitor or inhibitors under investigation, whereby each component is provided in separate containers or any combination of the components is provided in a single container. The kit may optionally contain the apparatus and one or more containers for obtaining and storing the sample prior to and during analysis and suitable buffers and other reagents to facilitate nucleic acid hybridization, synthesis, amplification and detection.

Therefore, it is an object of the present invention to provide sensitive methods for detecting drug resistance to reverse transcriptase inhibitor in a retrovirus-infected sample.

It is a further object of the present invention to provide a method for detecting drug resistance that is rapid, reliable, sensitive, and not labor intensive.

It is a further object of the present invention to provide a drug resistance assay that is phenotypic, not genotypic.

It is a further object of the present invention to provide an assay for drug resistance in which only a small amount of sample is needed for highly sensitive analysis.

It is a further object of the invention to provide an assay for the direct testing of biological body fluid samples such as serum, plasma, cerebrospinal fluid, saliva, semen and the like without extensive concentration, culturing or other processing techniques that would be required to increase the levels of reverse transcriptase in the sample under analysis.

It is a further object of the invention to provide an assay for drug resistance of a retrovirus that does not involve detection or amplification of the nucleic acid molecules of the retrovirus.

These and other objects, features, and advantages of the present method and kit will become apparent after a review of the following detailed description of the disclosed embodiments and the appended claims.

DETAILED DESCRIPTION OF THE DISCLOSED EMBODIMENTS

Figure 1A:
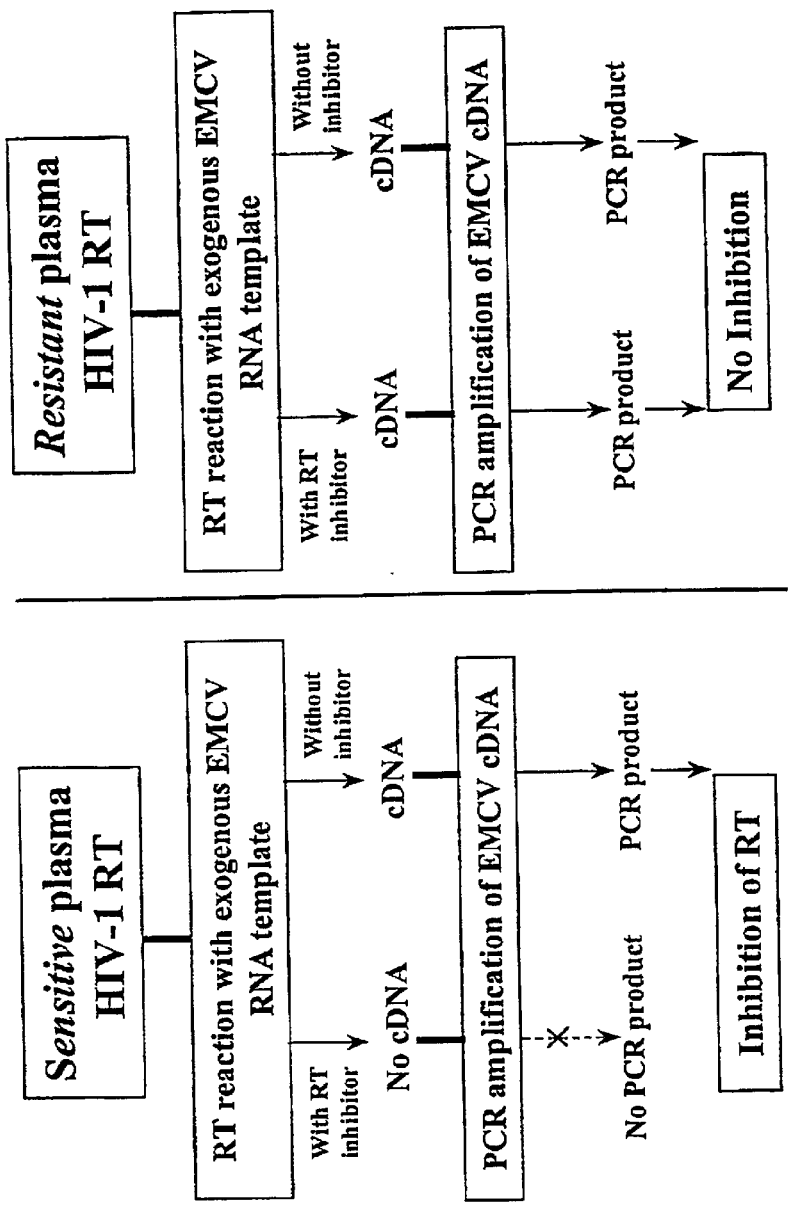
FIG. 1A is a flow chart depicting a phenotypic assay for the analysis of plasma HIV-1 resistance to the antiviral drugs 3TC, ddC, ddI, AZT, and NVP.

An assay and kit for the detection and monitoring of antiviral drug resistance of a retrovirus in a biological sample are provided. The assay is a non-culture, PCR-based phenotypic assay for the detection of drug resistant reverse transcriptase enzyme in the sample. The assay is useful for monitoring a patient's response to treatment with reverse transcriptase inhibitors so that, if resistance to a particular antiviral drug is detected, the treatment can be modified, even before actual symptoms of resistance are observed, thereby keeping viral replication and the onset of opportunistic infection and disease at a minimum. The assay is also useful for isolating and identifying new antiviral drug-resistant retroviral strains and for detecting the transmission of antiviral drug-resistant retroviral strains from patient to patient.

The phenotypic assay is based on the direct analysis of the susceptibility of reverse transcriptase in the sample to inhibition by a reverse transcriptase inhibitor drug such as, but not limited to, zidovudine (ZDV, also known as azidothymidine or AZT), didanosine (ddI), zalcitabine (ddC), lamivudine (3TC), stavudine (d4T), nevirapine (NVP), abacavir (ABC), delavirdine (DLV), loviride (LVD), efavirenz (EFV) or adefovir (bis-POM PMEA).

The reverse transcriptase phenotype is based on the level of inhibition of reverse transcriptase by a fixed concentration of drug, and is determined after calculation of the ratio of units of reverse transcriptase activity/ml from a reverse transcriptase reaction made in the presence of drug to reference reactions in the absence of drug (×100). Drug concentrations resulting in 50% or 90% inhibition ($IC_{50}$ and $IC_{90}$) may also be determined by testing the reverse transcriptase with increasing concentrations of drug. The level of inhibition of reverse transcriptase by drug is used to define the susceptibility of the retrovirus to the drug.

The terms "a", "an" and "the" as used herein are defined to mean "one or more" and include the plural unless the context is inappropriate.

The biological sample to be tested may be taken from an individual, such as a wound, blood, secretion, tissue, bone, muscle, cartilage, or skin sample or may be a laboratory research sample such as a cell culture supernatant, viral isolate or viral concentrate. The sample may be may be obtained from any biological source and is preferably taken from a human or animal capable of being infected with or harboring a retrovirus. For example, the sample may be a biological fluid, such as whole blood, blood serum, blood plasma, vaginal lavage, semen, urine, saliva, sputum, cerebrospinal fluid, lacrimal fluid, fermentation fluid, lymph fluid, tissue culture fluid, ascites fluid, synovial fluid, pleural fluid, and the like. The preferred biological sample is a biological fluid from which cells can be removed. The most preferred samples are blood plasma or serum. The sample is collected or obtained using methods well known to those skilled in the art.

The sample may be diluted, purified, concentrated, filtered, dissolved, suspended or otherwise manipulated prior to use in the assay. Preferably, a sample containing particulate matter is diluted, filtered, or both diluted and filtered prior to use. One feature of the present assay is that it is useful for the direct analysis of drug resistance from a biological body fluid sample such as blood serum or plasma, saliva, cerebrospinal fluid and similar body fluids. Therefore, such a sample need not be processed prior to being combined with the assay reagents, thereby facilitating sample analysis and minimizing the amount of labor, materials, time and expenses involved in performing the assay. The sample size for the biological fluid sample is preferably between approximately 0.5 μl and 1 ml.

The retrovirus present in the sample, or infecting the human or animal from which the sample is taken, is a virus characterized by the presence of reverse transcriptase, which transcribes the viral genomic RNA into a double-stranded DNA copy. Exemplary retroviruses for which a determination of drug resistance is sought include lentiviruses such as HIV-1 and HIV-2 and oncoviruses such as human T lymphocytic virus types I and II (HTLV-1 and HTLV-II). It will be understood by those skilled in the art that assays for retroviral drug resistance in species other than humans, such as nonhuman primates, cats, pigs, horses, and mice are included within the scope of the assay described herein.

The enzymatic activity of the reverse transcriptase enzyme of a retrovirus in the sample is determined by measuring the DNA product produced when an RNA template and a first complementary DNA primer from a suitable region of the encephalomyocarditis virus genome are incubated with a biological sample containing reverse transcriptase in the presence one or more drugs to which resistance is being determined, or drug homologs. As a comparative control, the enzymatic activity of the reverse transcriptase enzyme is also determined in the absence of the reverse transcriptase inhibitor. A comparison of these results provides confirmation of drug resistance and an indication as to the extent of resistance.

The concentration of drug added to the assay depends on the drug employed and the concentration of drug normally administered to a patient. For example, the concentration of 3TC added to an assay for a determination of 3TC resistance is preferably between approximately 1 and 10 μM, most preferably approximately 5 μM. The preferred concentration of nevirapine used in the assay is between approximately I and 100 μM, most preferably approximately 50 μM. It will be understood that suitable concentrations for other reverse transcriptase inhibitors can be calculated or experimentally determined using methods known to those skilled in the art.

The term "suitable region" is defined herein as a region of the RNA sequence having no significant secondary structure, less than 50% G-C content and to which complementary DNA primers can be generated which have Tm values within the range of reaction temperatures appropriate for the synthesis of a DNA strand, as described below. The RNA template can be of a length sufficient to produce a DNA product ranging in size from 100 to 500 base pairs in length, most preferably approximately 300 base pairs in length. The RNA template is most preferably the ribonucleotide of SEQ ID NO:4, which has the following sequence:

5' CAUUAGCCAU UUCAACCCAU GCGUUUGAGG AGAAGCGCUU 40
UCUGAUAACC GGUGGU-CUCC CAUCAGGUUG UGCAGCGACC 80
UCAAUGCUAA ACACUAUAAU GAAUAAUAUA AUAAUUAGGG 120
CGGGUUUGUA UCU-CACGUAU AAAAAUUUUG AAUUUGAUGA 160
UGUGAAGGUG UUGUCGUACG GAGAUGAUCU CCUUGUGGCC 200
ACAAAUUACC AAUUGGA-UUU UGAUAAGGUG AGAGCAAGCC 240 UCG-CAAAGAC AGGAUAUAAG AUAACUCCCG CUAACACAAC 280 UUCUACCUU CCUCU-UAAUU CGACGCUUGA AGACGUUGUC 320
UUCUUAAAAA GAAAGUUUAA GAAAGAGGGC CCUCUGUAUC 360
GGCCUGUCAU GAAC 3'

The incubation mixture is reacted or incubated under conditions whereby the RNA template and the DNA primer will anneal and a DNA strand will be synthesized as an extension from the DNA primer if the reverse transcriptase in the sample is resistant to and therefore not inhibited by the drug. The DNA product is amplified using a second complementary DNA primer from the encephalomyocarditis virus genome and suitable DNA amplification reagents and conditions, and the amplified product detected in accordance with methods known to those skilled in the art. Detection of the amplified DNA indicates resistance to the drug employed in the assay.

As used herein, the term "complementary DNA primer" means an oligonucleotide which anneals to the RNA template in a particular orientation to allow for the synthesis of a nascent DNA strand in the presence of reverse transcriptase in the biological sample under the conditions described herein. Also as used herein, the "condition" under which a DNA strand is synthesized include the presence of nucleotides, cations and appropriate buffering agents in amounts and at temperatures such that the RNA template and the DNA primer will anneal and oligonucleotides will be incorporated into a synthesized DNA strand if reverse transcriptase is not inhibited by the reverse transcriptase inhibitor drug. Exemplary conditions are set forth in the examples below. The described conditions have been optimized from other known RT/cDNA synthesis protocols. It is generally known that other conditions can be established for optimization of a particular reverse transcriptase reaction on the basis of protocols well known to one of ordinary skill in the art. The DNA primer can be the reverse primer of a primer pair to be used in a subsequent amplification, such as, for example, the oligonucleotide of SEQ ID NO:2 (EMCR2), which has the following sequence:

5' GTTCATGACA GGCCGATACA GAGG 3'

Preferably, the second DNA primer consists of the oligonucleotide of SEQ ID NO: 1, which has the following sequence: 5' CATTAGCCAT TTCAACCCAT 3'

The synthesized strand can be amplified by any of the amplification protocols known in the art now or in the future, including but not limited to the polymerase chain reaction (PCR), the ligation amplification reaction (LAR), the ligase-based amplification system (LAS), the self-sustained sequence replication (3SR) system, the transcription-based amplification system (TAS), and the Qβ replicase amplification method. The preferred amplification method is PCR.

For amplification by PCR, the conditions for amplification can include 30–40 cycles (preferably 35 cycles) of heating the synthesized DNA and primer pair to 93 to 97° C. (preferably 95° C.) for 30 to 90 seconds (preferably one minute), at 53 to 57° C. (preferably 55° C.) for 30 to 90 seconds (preferably one minute), and at 70 to 74° C. (preferably 72° C.) for 30 to 90 seconds (preferably one minute). The amplified synthesized DNA is preferably detected by an enzyme linked immunosorbent assay (ELISA). Alternatively, the amplified DNA is detected by Southern blot hybridization methods.

As used herein, the term "primer pair" refers to two primers, one having a forward designation and the other having a reverse designation relative to their respective orientations on a double-stranded DNA molecule which consists of a sense and antisense sequence, such that under the amplification conditions described herein, the forward primer anneals to and primes amplification of the sense sequence and the reverse primer anneals to and primes amplification of the antisense sequence. Primers can be selected for use in the amplification reaction on the basis of having less than 50% G-C content, having minimal complementarity with other primers in the reaction (to minimize the formation of primer dimers) and having Tm values with the range of reaction temperatures appropriate for the amplification method, preferably PCR. In addition, primers can be selected to anneal with specific regions of the RNA template such that the resulting DNA amplification product ranges in size from 100 to 500 base pairs in length and most preferably around 300 base pairs in length. For example, in the conditions described above, the primer pair can consist of the oligonucleotide of SEQ ID NO:1 (EMCF1) as the forward primer and the oligonucleotide of SEQ ID NO:2 (EMCR2) as the reverse primer.

As used herein, the terms "detecting" or "detection" of the amplified DNA refers to qualitatively or quantitatively determining the presence of the amplified DNA strand, which is only synthesized if reverse transcriptase is resistant to the reverse transcriptase inhibitor drug added to the assay mixture. The amplification of the synthesized DNA can be detected by any method for the detection of DNA known in the art. For example, detection of the amplified DNA can be by Southern blot hybridization assay, by visualization of DNA amplification products of specific molecular weight on ethidium bromide stained agarose gels, by measurement of the incorporation of radiolabeled nucleotides into the synthesized DNA strand by autoradiography or scintillation measurement, by ELISA modified for the capture of a detectable moiety bound to the amplified DNA, or any other detection method known to one of ordinary skill in the art. The preferred detection method is by hybridization of the amplified DNA to an internal specific oligoprobe using techniques such as ELISA. Southern blot hybridization or similar method, most preferably using the specific hybridization probe of SEQ ID NO:3, which has the following sequence:

5' TGCTCTCACC TRATCAAAAT CCAAT 3'

Additionally provided is a kit for determining reverse transcriptase inhibitor drug resistance in a biological sample. The kit contains a suitable region of the encephalomyocarditis virus genome as an RNA template, a first complementary DNA primer for reverse transcriptase, and a second complementary DNA primer for amplification via the polymerase chain reaction, whereby each component is provided in separate containers or any combination of the components is provided in a single container. The kit may optionally contain a sample of the drug to which resistance is being determined, a hybridization probe for detection of the amplified DNA product, an apparatus for conducting the assay, an apparatus for assay detection, one or more containers for obtaining and storing the sample prior to and during analysis, and suitable buffers and other reagents to facilitate nucleic acid hybridization, synthesis, amplification and detection.

A preferred embodiment of the assay method described herein for the detection of 3TC-, ddC-, ddI-, AZT-, and NVP-resistant HIV-1 reverse transcriptase activity in plasma is shown as a flow chart in FIG. 1A. The protocol for the assay is set forth in FIG. 1B. The preferred assay, also referred to as the Amp-RT assay, is also described in copending application, Ser. No. 08/763,762, which is incorporated by reference herein.

In contrast to culture-based phenotypic assays, the reverse transcriptase-based phenotypic assay described herein is a highly sensitive, rapid and simple method for the direct analysis of phenotypic resistance to reverse transcriptase inhibitor drugs, and therefore provides a feasible tool for clinical monitoring and management of drug resistance. The assay is useful for the determination of phenotypic resistance to both known and unknown genotypic mutations. This assay approach is expandable to analysis of resistance to a wide variety of reverse transcriptase inhibitor drugs, and may also be useful for surveillance of transmission of drug-resistant viruses.

EXAMPLE 1

Determination of Phenotypic Resistance to 3TC

This example describes the use of a rapid nonculture-based assay for the analysis of phenotypic resistance to 3TC in plasma HIV-1. The assay, referred to as the Amp-RT assay, was based on the direct analysis of the susceptibility of plasma HIV-1 reverse transcriptase to inhibition by 3TC-TP. The assay successfully detected phenotypic resistance to 3TC in plasma samples from 3TC-treated patients. Resistance to 3TC in HIV-1 reverse transcriptase carrying mutations associated with multidrug (MD) resistance to nucleoside analogs were also identified.

Materials and Methods

The phenotypic assay used in this example was based on the analysis of the susceptibility of HIV-1 reverse transcriptase activity from plasma to inhibition by 3TC-TP. Susceptibility of plasma reverse transcriptase to 3TC-TP was determined based on the level of inhibition produced by 3TC-TP, and was measured by running quantitative assays in the presence and absence of 3TC-TP.

The assay detects reverse transcriptase activity by using a nonretroviral heteropolymeric RNA template derived from the encephalomyocarditis virus (EMCV) genome, and a complementary EMCV-specific DNA oligoprimer. The RT-generated EMCV cDNA is detected by PCR amplification and internal oligoprobing of the PCR product with an EMCV-specific probe.

Figure 1B:
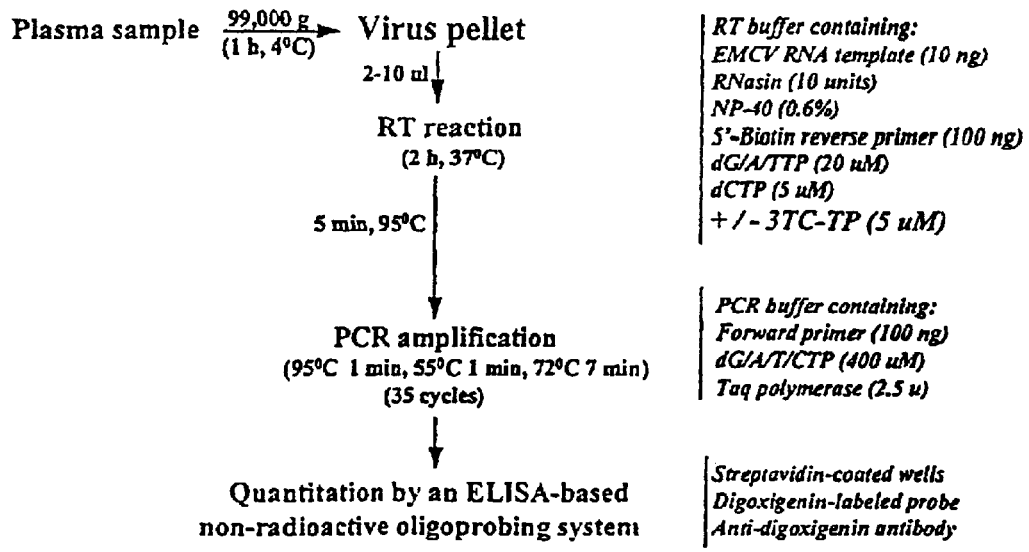
FIG. 1B is a flow chart depicting a protocol for the rapid analysis of HIV-1 resistance to 3TC using the reverse transcriptase-based phenotypic assay.

For culture supernatant, 10 $\mu$l were directly used for the reverse transcriptase reaction. The analysis of phenotypic resistance in plasma samples was made in plasma-free virus pellets as described in the protocol set forth in FIG. 1B. A volume of 100 $\mu$l of EDTA plasma was clarified by centrifugation at 10,000 g for five minutes, and then ultracentrifuged at a fixed angle at 99,000 g for one hour at 4° C. The viral pellet was resuspended in 100 $\mu$l of reverse transcriptase buffer (50 mM Tris-HCl, 50 mM KCl, 10 MM $MgCl_2$), and aliquots of 2 to 10 $\mu$l were used for the analysis of phenotypic resistance.

For quantitation of reverse transcriptase levels, a standard curve was generated by using known reverse transcriptase units from a reference HIV-1 stock (Virology Quality Assurance Laboratory, Rush-Presbyterian-St. Luke's Medical Center, Chicago, Ill.). This virus stock was shown to have $0.96 \times 10^{-10}$ units of reverse transcriptase activity/virion. Quantitative detection of Amp-RT products was made by using an ELISA-based, nonradioactive, oligoprobing system with an internal EMCV-specific probe. The results of Amp-RT signals were expressed as units of reverse transcriptase activity per milliliter, and reflect the average of duplicate or triplicate results. Qualitative detection of Amp-RT products was made by Southern blot hybridization to a $^{32}$P-end-labeled EMCP1 probe.

Phenotypic resistance of HIV-1 to 3TC was measured by the Amp-RT assay. Amp-RT detects reverse transcriptase activity by using a heterologous RNA template derived from the encephalomyocarditis virus (EMCV), a complementary DNA oligoprimer, and PCR amplification of reverse transcriptase-generated EMCV cDNA. For the phenotypic analysis of 3TC resistance, 10 $\mu$l of culture supernatant or virus pellets from 2 to 10 $\mu$l of plasma were applied in duplicate to a reverse transcriptase buffer containing 10 ng of EMCV RNA template, 10 units of RNasin, 0.6% NP-40, 100 ng of the 5'-biotin-labeled EMCR2 antisense primer, 1 mM EGTA, 2 mM dithiothreitol, 50 mM Tris-HCl, 50 mM KCl and 10 mM $MgCl_2$, 20 $\mu$M of dATP, dGTP and dTTP, 5 $\mu$M of dCTP. To determine the susceptibility of the reverse transcriptase to 3TC-TP, an additional Amp-RT reaction was made in the presence of 3TC-TP, with concentrations of 3TC-TP ranging from 0.1 to 10 $\mu$M. The reactions were incubated at 37° C. for two hours and heated at 95° C. for five minutes to destroy reverse transcriptase activity. PCR amplification of reverse transcriptase products was made as follows after the addition of 200 $\mu$M of each dNTP. A volume of 50 $\mu$l of PCR buffer containing 2.5 units of Taq polymerase, 100 ng of the sense primer EMCF1, and 200 $\mu$M of each dNTP was added to the reverse transcriptase mixture. The reaction was cycled 35 times at 95° C. for one minute, 55° C. for one minute, and 72° C. for one minute.

As described above, for quantitation of reverse transcriptase levels, a standard curve was generated by using known virion numbers of the reference HIV-1 virus stock. The method described by Garcia Lerma et al., *J. Infect. Dis.* 1998;177:1221–1229 was used for characterization of the reverse transcriptase activity in the reference virus as well as the quantitation of Amp-RT products by an ELISA-based non-radioactive oligoprobing system. The samples were considered as positive when duplicate test results were positive. Qualitative detection of Amp-RT products was made by an ELISA-based non-radioactive oligoprobing system as described in FIG. 1B and by Heneine et al., *J. Infect. Dis.* 1995;171:1210–1216.

Susceptibility of HIV-1 reverse transcriptase to 3TC-TP was determined from the level of inhibition of reverse transcriptase activity by 3TC-T?. The percentage of inhibition was calculated by using the ratio of reverse transcriptase level obtained in Amp-RT reactions containing 3TC-TP to that seen in Amp-RT reactions made in the absence of 3TC-TP (×100). Drug concentrations resulting in 50% and 90% inhibition ($IC_{50}$ and $IC_{90}$) were also determined by testing reverse transcriptase in the presence of several 3TC-TP concentrations.

Detection of 3TC-resistance Mutations

Genotypic resistance to 3TC was analyzed by sequencing and/or by the genotyping HIV-1 Line probe assay (LiPA) to detect mutations at codon 184. This assay is based on reverse hybridization of a biotinylated PCR fragment with short, immobilized oligonucleotides as described by Stuyver et al., *Antimicrob. Agents Chemother*. 1997;41:284–291. A region of the HIV-1 reverse transcriptase comprising amino acid 19 to 233 was sequenced in selected samples.

Study Population

A total of 30 EDTA-plasma samples from 15 HIV-1-infected patients from the Veteran Administration Medical Center, Decatur, Ga., were studied. The samples were collected from patients before and during anti-retroviral therapy with 3TC. The Amp-RT-based phenotypic assay was done under code with respect to date of serial bleed and reverse transcriptase genotype. One plasma specimen from a blood donor who tested antibody negative for HIV-1/2, HTLV-I/II was used as an assay negative control.

Viruses and 3TC-5'-triphosphate (3TC-TP)

For assay development and validation, HIV-1 molecular infectious clones (MIC) xxBRUpitt and M184Vpitt were used as wild type (WT) and 3TC-resistant (M184V mutation) HIV-1 reference viruses, respectively. Other reference viruses (controls) included M184V/Y181CEU, Y181CEU, and HIV-1$_{RTMC}$/MT-2, representing 3TC and nevirapine-resistant (M184V/Y181C), nevirapine-resistant (Y181C), and AZT-resistant (D67N/K70R/T215F/K219Q) HIV-1, respectively as described by Larder and Kemp, *Science* 1989;246:1155–1158. Wild type HIV-1$_{SUM9}$, and multiple dideoxy nucleoside-resistant HIV-1$_{SUM8}$ (Q151M mutation), HIV-1$_{SUM12}$ (F77L/F116Y/Q151M) and HIV- 1$_{SUM13}$ (A62V/V75I/F77L/F116Y/Q151M) MICs were provided by Dr. Mitsuya as described by Shirasaka et al., *Proc. Natl. Acad Sci. USA* 1995;92:2398–2402. The synthesis and preparation of 3TC-TP were carried out as described by Schinazi et al., *Antimicrob. Agents Chemother.* 1992;36:2423–2431. The crude 3TC-5-TP was purified by FPLC using a HiLoad 26/10, Q Sepharose Fast Flow™ Pharmacia chromatography column (Pharmacia, Piscataway, N.J.) and gradient of TEAE buffer (pH 7.0). The compound was characterized by UV, proton and phosphorous NMR, mass spectroscopy and high pressure chromatography. The concentration of 3TC-TP resulting in 50% inhibition of incorporation of 3HdCTP into a (rI)n-dC12–18 template primer by recombinant p66/p51 HIV-1 reverse transcriptase (Biotechnology General, Rehovot, Israel) was 1.3 $\mu$M as determined by decrease in the formation of acid insoluble product compared to untreated control.

Results

Amp-RT Testing Conditions that Differentiates Between Wild Type and 3TC-resistant HIV-1

Inhibition of reverse transcriptase by 3TC-TP results from the ability of 3TC-TP to act as a competitive inhibitor for 2'-deoxycytidine-5'-triphosphate (dCTP) and chain terminator as described by Arts and Wainberg, *Antimicrob. Agents Chemother.* 1996;40:527–540. To determine the optimal ratio of 3TC-TP and dCTP needed to inhibit wild type HIV-1 reverse transcriptase, but not 3TC-resistant reverse transcriptase, reverse transcriptases were tested from a wild type (xxBRUpitt) and a 3TC-resistant (M184Vpitt) HIV-1 in the presence of increasing concentrations of 3TC-TP (from 0.1 to 10 $\mu$M) and a fixed concentration of dCTP (5 $\mu$M). The 5 $\mu$M dCTP was the lowest concentration found that did not compromise the sensitivity of the Amp-RT assay.

Figure 2A:
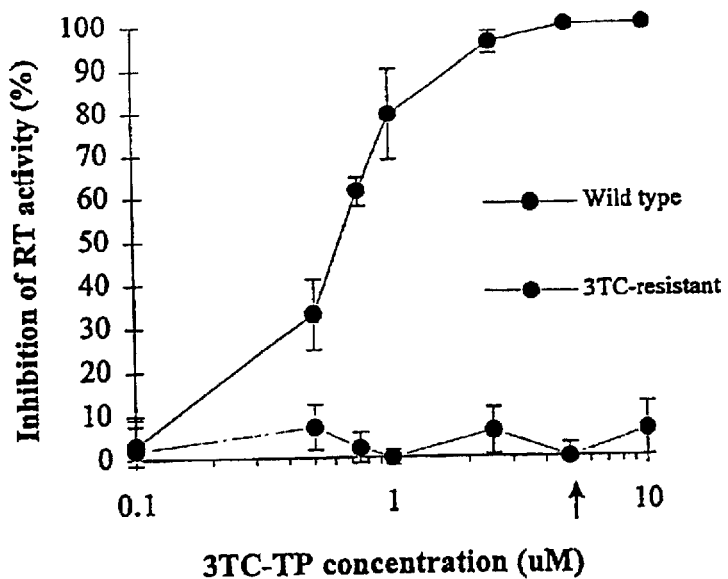
FIG. 2A is a graph showing the concentration of 3TC-triphosphate (3TC-TP) versus inhibition of reverse transcriptase activity in wild type (xxBRU$_{pitt}$) and 3TC-resistant (M184V$_{pitt}$) HIV-1. The arrow indicates the 3TC-TP concentration that differentiates between wild type and 3TC-resistant RT based on the level of RT inhibition.
Figure 2B:
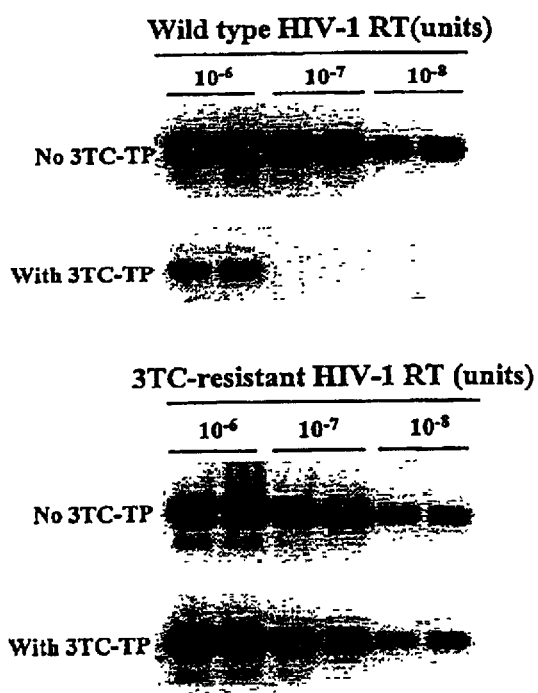
FIG. 2B is a schematic representation of electrophoretic gels showing ten-fold serial dilutions of both wild type (xxBRU$_{pitt}$) and 3TC-resistant (M184V$_{pitt}$) HIV-1, tested in the presence and absence of 3TC-TP. A concentration of 5 $\mu$M 3TC-TP distinguishes between wild type and 3TC-resistant RT within a wide range of RT levels.

FIGS. 2A and 2B illustrate the inhibition seen with $10^{-7}$ units of reverse transcriptase activity, and shows that complete inhibition of the reverse transcriptase from the wild type, but not from the 3TC-resistant virus, was accomplished at 5 $\mu$M of 3TC-TP. This concentration of 3TC-TP was able to inhibit completely $10^{-7}$ and $10^{-8}$ units of reverse transcriptase activity from the wild type HIV-1, the equivalent to $10^5$ and $10^4$ HIV-1 particles/ml of the reference virus, respectively as shown in FIG. 2. With a higher input of reverse transcriptase ($10^{-6}$ units of reverse transcriptase activity; the equivalent to $10^6$ HIV-1 particles/ml of the reference virus), these conditions did not result in complete inhibition. The residual reverse transcriptase activity in the Amp-RT reaction containing 3TC-TP was found to be 0.4% of the Amp-RT signal from the control reaction that had no 3TC-TP. This reduction in reverse transcriptase signal is equivalent to a 2.35 $\log_{10}$ drop in Amp-RT virus load. No significant inhibition was seen in the 3TC-resistant HIV-1 tested at either high or low input of reverse transcriptase, demonstrating the ability of the assay to distinguish between wild type and 3TC-resistant reverse transcriptases within a wide range of reverse transcriptase levels. Based on these results, Amp-RT conditions containing 5 $\mu$M 3TC-TP as a primary screening assay for 3TC resistance was used in all testing unless otherwise indicated.

Figure 3:
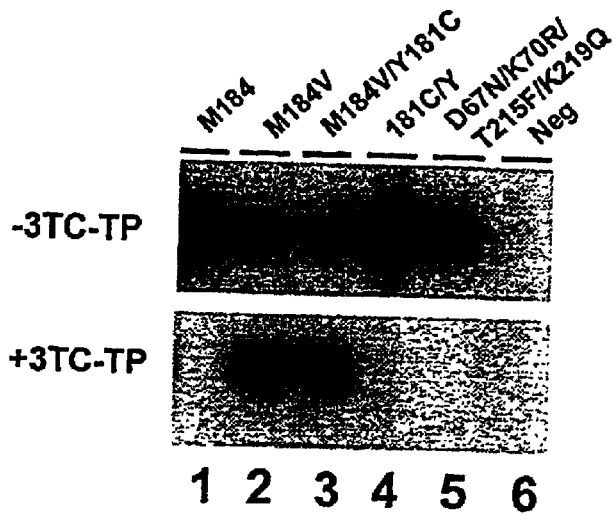
FIG. 3 is a schematic representation of electrophoretic gels showing inhibition by 3TC-TP of HIV-1 having 3TC-, nevirapine- or AZT-resistance mutations. Lane 1 is wild type (xxBRU$_{pitt}$) HIV-1; lane 2 is 3TC-resistant (M184V$_{pitt}$) HIV-1; lane 3 is 3TC/nevirapine-resistant (M184V/Y181C$_{EU}$)HIV-1; lane 4 is nevirapine-resistant (181C/Y$_{EU}$) HIV-1; lane 5 is AZT-resistant (HIV-1$_{RTMC}$/MY-2) HIV-1; lane 6 is the negative control.

To demonstrate that the Amp-RT-based phenotypic assay was specific for 3TC resistance, several HIV-1 reference viruses well-characterized phenotypic resistance to nucleoside and non-nucleoside analogs were tested. FIG. 3 shows that resistance to 3TC was only seen in reverse transcriptases carrying the M184V mutation. As expected, HIV-1 reverse transcriptases carrying AZT (D67N, K70R, T215F, K219Q) or nevirapine (Y181C) resistance mutations were all found to be susceptible to 3TC-TP. These results confirm that the assay was specific for viruses with phenotypic resistance to 3TC, and indicate that the presence of other mutations associated with AZT and nevirapine resistance does not affect the inhibition of reverse transcriptase activity by 3TC-TP.

Assay Detection Threshold for Phenotypic Resistance to 3TC

Figure 4:
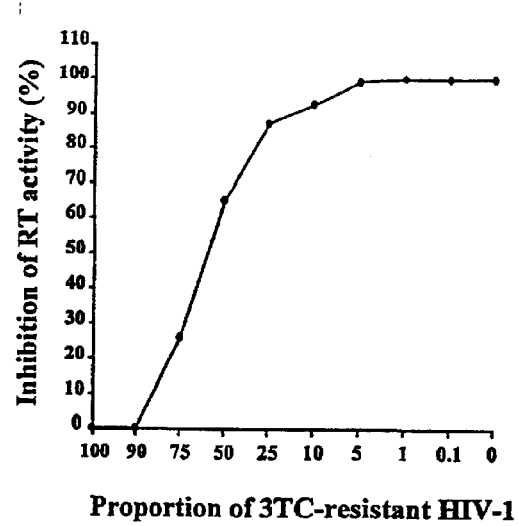
FIG. 4 is a graph showing the proportion of 3TC-resistant (M184V$_{pitt}$) HIV-1 in a background of wild type (xxBRU$_{pitt}$) HIV-1 versus inhibition of RT activity by 3TC-TP (5 $\mu$M).

The assay detection threshold for 3TC resistance was tested by mixing the wild type (xxBRUpitt) and 3TC-resistant (M184Vpitt) MIC at different proportions and testing for evidence of 3TC resistance. The reference viruses were adjusted to similar levels of reverse transcriptase activity before virus mixtures were prepared. The level of inhibition of reverse transcriptase activity by 3TC-TP observed in each mixture with the proportion of 3TC-resistant virus used was compared. FIG. 4 shows that the assay detection threshold was found to be 10% of 3TC-resistant viruses in a background of wild type HIV-1. A good correlation between the proportion of viruses carrying the M184V mutation and the level of inhibition was also observed. For instance, in mixtures containing 25% or 75% of 3TC-resistant virus, the observed inhibition was 87% and 26%, respectively, which very likely represents the signals from the 3TC-resistant reverse transcriptase and, therefore suggests that only wild type reverse transcriptase activity was inhibited.

The same mixtures were used to compare the detection threshold of the Amp-RT-based phenotypic assay with the genotypic detection threshold for viruses carrying the M184V mutation by the LiPA assay as shown in FIG. 4. The detection threshold of 3TC-resistant virus by the HIV-1 LiPA assay was 10%, indicating that both assays can reliably detect low levels of either genotypic or phenotypic resistance to 3TC. However, signal intensities in mixtures containing 50% wild type and 50% 3TC-resistant virus were not similar in the LiPA assay. This may be due to different levels of HIV-1 RNA in both reference viruses resulting from adjustment of virus by reverse transcriptase activity rather than by RNA levels or to different efficiencies in the hybridization of the wild type or 184V-specific probes.

Multi-drug Resistance Mutations Confer Phenotypic Resistance to 3TC

Mutations in codon 151 of the HIV-1 reverse transcriptase have been associated with resistance to several dideoxynucleoside analogs including AZT, ddC, ddI and d4T. HIV-1 containing mutations associated with MD resistance to several dideoxynucleoside analogs were analyzed to determine if mutations other than 184V confer resistance to 3TC. The Amp-RT IC50 and IC90 values for 3TC of viruses containing one (Q151M; HIV-1SUM 8), three (F77L/F116Y/Q151M; HIV-1SUM 12), and all five mutations associated with MD resistance (A62V/V75I/F77L/F116Y/Q151M; HIV-1SUM 13) were determined. Control wild type HIV-1 reverse transcriptases were also tested.

The reverse transcriptase from HIV-1 carrying the Q151M mutation had a slightly reduced susceptibility to 3TC, with $IC_{50}$ and $IC_{90}$ values approximately two-fold higher than those of reverse transcriptase reference viruses. However, the presence of additional multidrug (MD) resistance mutations resulted in higher levels of resistance to 3TC, with an increase in $IC_{50}$ values of six- and eight-fold for virus with three or all five MD resistance mutations, respectively, compared to wild type virus which had similar $IC_{50}$ and $IC_{90}$ values for 3TC-TP. These results suggest that these multidrug resistance mutations in HIV-1 reverse transcriptase confer phenotypic resistance to 3TC.

Analysis of Phenotypic Resistance to 3TC in Plasma HIV-1 RT and Correlation with Mutations at Codon 184

The performance of the Amp-RT-based phenotypic assay with plasma samples was evaluated by testing 30 specimens collected from 15 HIV-1-infected patients before and during treatment with 3TC. The results are shown in Tables 1 and 2 below. All pretreatment samples (n=12) had wild type phenotypes, with reverse transcriptase inhibition values of greater than 95%. The observed inhibition in these samples ranged from 95.9% to 100% (mean=98.7%+1.8%; median=99.8%). Of these samples, 11 had wild type genotypes at codon 184 and one had a mixture of wild type and M184I (sample 7A). Mutations at codon 69, which is associated with resistance to ddC, were observed in samples from the two individuals who had lower susceptibility to 3TC-TP (samples 13A and 15A; reverse transcriptase inhibition values of 95.9% and 95.5%, respectively). The T69D mutation has been recently shown to confer low cross-resistance to 3TC (12-fold), and therefore, may be responsible for the decreased susceptibility to 3TC observed in these samples with the Amp-RT assay.

Figure 5:
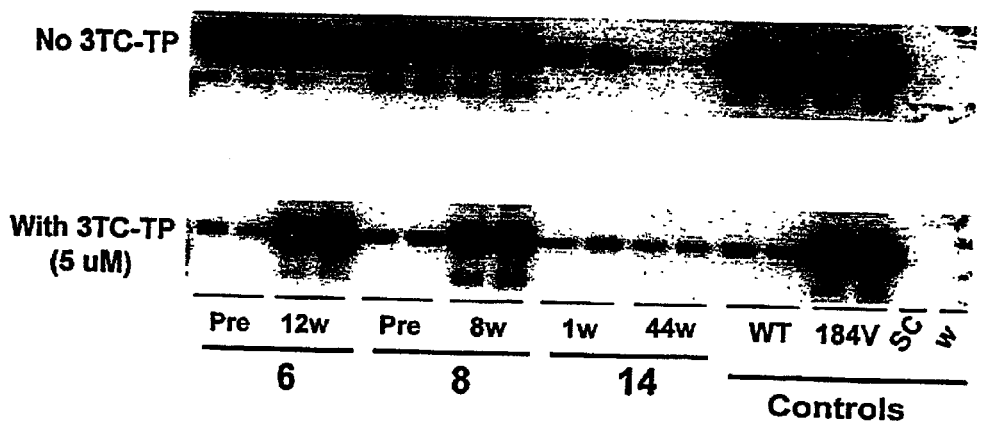
FIG. 5 is a schematic representation of electrophoretic gels showing inhibition by 3TC-TP of HIV-1 RT from plasma of three HIV-1-infected patients before and during therapy with AZT plus 3TC. Lane SC is HIV-1/2, HTLV I/II seronegative control. Lane W is water control.

In contrast, values of reverse transcriptase inhibition of less than 95% were only seen in samples obtained from patients after 1 to 60 weeks of antiretroviral therapy with 3TC (n=18). Of these samples, 12 had the M184V mutation, four had mixtures of wild type and M184V genotypes, and two (samples 10A and 14A) had only wild type genotypes. The mean inhibition in the samples with evidence of 184V only was 30.8% (median=24.9%), reflecting the high level of resistance to 3TC. The mean inhibition in samples with mixtures of wild type and resistant genotypes was 49.3% (median=52.4%), indicating lower levels of resistance, which was expected since these samples have higher proportions of wild type reverse transcriptase. The lower level of resistance to 3TC observed in post-therapy samples was seen in specimens collected after one and four weeks of therapy (samples 14A and 10A; reverse transcriptase inhibition values of 94.7% and 87.8%, respectively). Both samples had wild type genotype at codon 184. However, sample 14A had a T69D mutation which may explain the borderline susceptibility to 3TC. The absence of detectable 184V mutation in sample 10A may represent an earlier detection of phenotypic resistance, or may be due to the inability of the sequencing and LiPA assay to detect a low proportion of 3TC-resistant viruses. Both patients had high levels of 3TC resistance in samples obtained after 12 and 44 weeks of 3TC treatment (Table 1). FIG. 5 illustrates representative results for plasma from three patients, and shows the presence of phenotypic differences between specimens collected before and during antiretroviral therapy with 3TC.

Conclusion

The efficacy of antiretroviral therapy with reverse transcriptase inhibitors such as 3TC is strongly limited by the emergence of drug resistant HIV-1 variants. The assay used in this example is a rapid nonculture-based assay for the analysis of phenotypic resistance to 3TC of plasma HIV-1 reverse transcriptase. The assay used a small volume of plasma, and the HIV-1 reverse transcriptase phenotype for 3TC was determined based on the level of reverse transcriptase inhibition by a single 3TC-TP concentration. Compared to standard culture-based phenotypic assays, this approach has several advantages. First, test results were obtained in one to two days, providing rapid information on resistance to 3TC that should be of clinical relevance to treatment decisions and patient management. Second, testing is directly made on reverse transcriptase from plasma and, therefore, unlike culture-based methods, the assay does not select for particular viral isolates. Third, the assay has a low detection threshold for 3TC-resistant reverse transcriptase and may be useful for the early detection of 3TC resistance.

The data generated in this example demonstrate that the assay can be used to successfully monitor for resistance to 3TC mediated by mutations at codon 184. Decreased reverse transcriptase inhibition by 3TC-TP occurred in samples obtained from persons after treatment with 3TC, and coincided with the emergence of resistant genotypes. In addition to providing phenotypic information on resistance to 3TC, the Amp-RT reaction done without 3TC-TP provided information on the reverse transcriptase-based plasma virus and, therefore, can be used to simultaneously monitor the virologic response to treatment with 3TC.

The assay was designed for rapid evaluation of resistance to 3TC and included testing with an optimal concentration of 3TC-TP. Using this assay format, an interesting association was found between mutations at codon 69 and borderline susceptibility to 3TC-TP, suggesting that this mutation may confer some level of resistance to 3TC. To further clarify the role of the observed borderline susceptibility in samples with mutations at codon 69 or others, the assay format can be modified to include testing with several concentrations of 3TC-TP to better quantitate the level of resistance to 3TC. In addition to clinical monitoring of 3TC resistance, the assay may also be used as a rapid method for surveillance of transmission of 3TC resistance among persons with newly diagnosed HIV-1 infections and for detection of resistance to 3TC in 3TC-naive HIV-1-infected patients.

TABLE 1

| Sample | Weeks | Treatment | RT activity (units/ml) No 3TC-TP | RT activity (units/ml) With 3TC-TP (5 μM) | Inhibition of RT (%) | Mutations Codon 184 | Mutations Others |
|---|---|---|---|---|---|---|---|
| $1_B$ | Pre | AZT/ddC | $1.7 \times 10^{-9}$ | n.d. | 100 | M184 | — |
| $1_G$ | 12 | AZT/3TC | $2.1 \times 10^{-6}$ | $5.1 \times 10^{-7}$ | 75.6 | V/M184 | L41; Y215 |
| $1_F$ | 18 | AZT/3TC | $1.3 \times 10^{-7}$ | $3.3 \times 10^{-8}$ | 75.9 | V184 | — |
| $2_B$ | Pre | AZT/ddC | $2.2 \times 10^{-6}$ | $6.3 \times 10^{-9}$ | 99.7 | M184 | — |
| $2_F$ | 12 | AZT/3TC | $1.5 \times 10^{-6}$ | $4.7 \times 10^{-7}$ | 68 | V184 | — |
| $3_B$ | Pre | AZT | $1.8 \times 10^{-6}$ | $1.7 \times 10^{-8}$ | 99.4 | M184 | — |
| $3_F$ | 12 | AZT/3TC | $1.6 \times 10^{-8}$ | $1.2 \times 10^{-9}$ | 92.3 | M/V184 | — |
| $3_G$ | 21 | AZT/3TC | $5.1 \times 10^{-9}$ | $1.0 \times 10^{-8}$ | 0 | V184 | — |
| $4_A$ | Pre | AZT | $1.6 \times 10^{-7}$ | $1.2 \times 10^{-10}$ | 99.9 | M184 | R70 |
| $4_B$ | 12 | AZT/3TC | n.d. | n.d. | — | V184 | R70 |
| $5_A$ | Pre | AZT | $1.2 \times 10^{-8}$ | n.d. | 100 | M184 | Y215 |
| $5_B$ | 4 | AZT/3TC | n.d. | n.d. | — | M/V184 | Y215 |
| $5_C$ | 10 | AZT/3TC | n.d. | n.d. | — | V184 | Y215 |
| $6_A$ | Pre | None | $7.7 \times 10^{-5}$ | $3.6 \times 10^{-8}$ | 99.9 | M184 | — |
| $6_B$ | 12 | AZT/3TC | $2.3 \times 10^{-5}$ | $1.5 \times 10^{-5}$ | 34.7 | V184 | — |
| $7_A$ | Pre | None | $1.2 \times 10^{-8}$ | n.d. | 100 | M/I184 | — |
| $7_C$ | 28 | AZT/3TC | n.d. | n.d. | — | V184 | — |
| $8_A$ | Pre | AZT | $4.4 \times 10^{-5}$ | $5.7 \times 10^{-8}$ | 99.9 | M184 | L41; Y215 |

TABLE 1-continued

| Sample | Weeks | Treatment | RT activity (units/ml) No 3TC-TP | RT activity (units/ml) With 3TC-TP (5 μM) | Inhibition of RT (%) | Mutations Codon 184 | Mutations Others |
|---|---|---|---|---|---|---|---|
| $8_B$ | 8 | AZT/3TC | $5.0 \times 10^{-5}$ | $4.3 \times 10^{-5}$ | 15 | V184 | L41; Y215 |
| $9_A$ | Pre | d4T | $2.9 \times 10^{-6}$ | $6.3 \times 10^{-8}$ | 97.8 | M184 | L41; Y215 |
| $9_F$ | 12 | AZT/3TC | $2.1 \times 10^{-6}$ | $1.1 \times 10^{-6}$ | 47 | V184 | L41; Y215 |
| $10_A$ | 4 | AZT/3TC | $8.9 \times 10^{-5}$ | $9.1 \times 10^{-6}$ | 87.8 | M184 | Y215? |
| $10_C$ | 12 | AZT/3TC | $1.9 \times 10^{-7}$ | $1.9 \times 10^{-7}$ | 0 | M/V184 | — |
| $10_G$ | 52 | AZT/3TC | $2.6 \times 10^{-5}$ | $3.5 \times 10^{-5}$ | 0 | V184 | L41; Y215 |
| $11_A$ | 12 | AZT/3TC | $1.9 \times 10^{-7}$ | $1.3 \times 10^{-7}$ | 29.1 | V/M184 | R70 |
| $11_C$ | 36 | AZT/3TC | $1.7 \times 10^{-7}$ | $7.0 \times 10^{-8}$ | 58.5 | V184 | R70 |
| $12_A$ | Pre | AZT | $2.5 \times 10^{-5}$ | $9.2 \times 10^{-7}$ | 96.3 | M184 | — |
| $12_B$ | 28 | AZT/3TC | $1.7 \times 10^{-6}$ | $5.1 \times 10^{-7}$ | 70 | V184 | R70; Y215 |
| $13_A$ | Pre | d4T | $1.5 \times 10^{-6}$ | $6.2 \times 10^{-8}$ | 95.9 | M184 | N69; R70 |
| $13_F$ | 60 | d4T/3TC/IND | $6.3 \times 10^{-5}$ | $7.4 \times 10^{-5}$ | 0 | V184 | L41; D/N69; R70 |
| $14_A$ | 1 | AZT/3TC | $2.5 \times 10^{-7}$ | $1.3 \times 10^{-8}$ | 94.7 | M184 | L41; D69; R70; Y215 |
| $14_F$ | 44 | IND/3TC | $2.9 \times 10^{-9}$ | $5.1 \times 10^{-9}$ | 0 | V184 | D69; R70; Y215 |
| $15_A$ | Pre | AZT | $8.9 \times 10^{-5}$ | $4.0 \times 10^{-6}$ | 95.5 | M184 | D69 |
| $15_D$ | 40 | AZT/3TC/IND | $1.6 \times 10^{-10}$ | $2.4 \times 10^{-10}$ | 0 | V184 | D69; Y215 | n.d. = not detected; IND = indinavir
Previous treatments were: patient 9 was on AZT before first sample; patient 13 was on AZT/ddC before first sample; and patient 14 was on ddi for a period of time between first and second sample

TABLE 2

Amp-RT Detection of Phenotypic Resistance Correlates to Mutations at Codon 184

| | Sensitive phenotype | | | Resistant phenotype* | | |
|---|---|---|---|---|---|---|
| | 184 wt | 184 wt-MT | 184 MT | 184 wt | 184 wt-MT | 184 MT |
| Pretreatment (n = 12) | 12 | 0 | 0 | 0 | 0 | 0 |
| 1–4 weeks (n = 2) | 0 | 0 | 0 | 2 | 0 | 0 |
| 4–12 weeks (n = 8) | 0 | 0 | 0 | 0 | 4* | 4 |
| >12 weeks (n = 8) | 0 | 0 | 0 | 0 | 0 | 8 |

*RT phenotype was determined based on the level of RT inhibition by 5 μM 3TC-TP.
wt-MT = a mixture of wild type and M184V

EXAMPLE 2

Determination of Phenotypic Resistance to Nevirapine

This example describes the use of a nonculture-based assay for the rapid analysis of phenotypic resistance to nevirapine in HIV-1 from plasma. The assay is based on the direct analysis of the susceptibility of plasma HIV-1 RT to inhibition by nevirapine. The assay used in this example was the PCR-based Amp-RT described in Example 1.

Materials and Methods

Susceptibility of plasma RT to nevirapine was determined based on the level of inhibition produced by the drug and was measured by running quantitative Amp-RT reactions in the presence and absence of nevirapine.

For culture supernatant, 10 μl were used directly in the Amp-RT assay. For plasma testing, a volume of 100 μl was clarified by centrifugation at 10,000 g for five minutes and then ultracentrifuged at a fixed angle at 99,000 g for 1 hour at 4° C. The viral pellet was resuspended in 100 μl of RT buffer (50 mM Tris-HCl, 50 mM KCl, 10 mM $MgCl_2$). Ten microliter aliquots of virus pellets were applied to an RT buffer containing 10 ng of EMCV RNA template, 10 units of RNasin, 0.6% NP40, 100 ng of the 5'-biotin-labeled EMCR2 antisense primer, 1 mM EGTA, 2 mM dithiothreitol, 50 mM Tris-HCl, 50 mM KCl, 10 mM $MgCl_2$, and 400 uM of each dNTP. Reactions were incubated at 37° C. for 2 hours and then heated at 95° C. for five minutes to destroy RT activity. PCR amplification of RT products was performed as previously described above in Example 1. The conditions for PCR were 35 cycles at 95° C. for one minute, 55° C. for one minute, and 72° C. for one minute.

For quantitation of RT levels, a standard curve was generated by using known RT units from a reference HIV-1 stock (Virology Quality Assurance Laboratory, Rush-Presbyterian-St. Luke's Medical Center, Chicago, Ill.). This virus stock, referred to as VQA, has been shown to have $0.96 \times 10^{-10}$ units of RT activity/virion. Quantitative detection of Amp-RT products was made by using an ELISA-based, nonradioactive, oligoprobing system with an internal EMCV-specific probe, as described by Garcia Lerma J. Infect. Dis. 1998;177:1221–1229. All samples were tested within the linear range of the Amp-RT assay (from $10^{-6}$ to $10^{-10}$ units of RT activity). Samples which had levels of RT activity above the linear range of the assay, were further diluted in RT buffer and retested again. The minimum detectable level of HIV-1 RT activity by the Amp-RT in plasma is $10^{-10}$ units, the equivalent of 1 HIV-1 particle of the reference virus used for quantitation. The results of Amp-RT signals were expressed as units of RT activity per milliliter of plasma and reflect the average of duplicate results.

Detection of Phenotypic Resistance to Nevirapine by the Amp-RT Assay

To determine the susceptibility of plasma HIV-1 RT to nevirapine, Amp-RT reactions were run in the absence and presence of nevirapine. Percentage of inhibition was calculated by using the ratio of RT level seen in the presence of nevirapine to that seen in Amp-RT reactions made in the absence of nevirapine (×100). Nevirapine concentrations resulting in 50% and 90% inhibition ($IC_{50}$ and $IC_{90}$) of RT activity were measured by testing RTs in the presence of several concentrations of nevirapine and were determined by non-linear regression as described by Shafer et al. J. Infect. Dis. 1995;172:70–78.

Detection of Mutations at Codon 181 of the HIV-1 RT Gene in Plasma Samples

Levels of Y181C mutation in plasma HIV-1 RT were previously determined by differential hybridization as described by Havlir et al. *J. Virol.* 1996;70:7894–7899. Briefly, viral RNA was amplified by RT-PCR using primers 5RT and 3RT. The resulting PCR product was added to streptavidine-coated wells and incubated at 50° C. for 30 minutes. After washing, a hybridization solution containing a specific probe for the Y181C mutation (MUT probe) was added and incubated for one hour at 45° C. To normalize for the amount of PCR product bound to each well, an additional probe to a highly conserved region of the HIV-1 RT (generic probe; GNR) was also used. Hybridization was measured by chemiluminiscence and results are expressed as MUT/GNR ratio. The threshold for considering detectable Y181C mutation has been defined by Havlir et al. 1996 as a MUT/GNR ratio of 0.03.

Quantitation of HIV-1 RNA Levels in Plasma

HIV-1 RNA levels in plasma samples were determined by an RT-PCR-based method (Roche Amplicor HIV Monitor Test), as specified by the manufacturer. The reported detection limit of the assay is 200 RNA copies/ml of plasma.

Study Population

A total of 30 plasma samples obtained from four HIV-1-infected patients (patients N12, N06, N07 and E01) were analyzed as described by Havlir et al. 1996. The four patients were enrolled in a double-blind clinical trial of nevirapine versus placebo at the University of California, San Diego. The daily dose of nevirapine was 200 mg for the first 14 days, and then 400 mg. A more detailed description of the study population was previously reported by Havlir et al. 1996.

Reference Viruses

For assay development and validation, HIV-1 isolates V818-5, S469-2/M3, X165-11, W786-6, X82-5, X4034, X165-6 and X267-1 were used. Susceptibility to nevirapine in these isolates was previously determined by a plaque-reduction assay as described by Havlir et al. 1996. Sequence analysis of the RT gene was done by standard methods as described by Mulder et al., *J. Clin. Microbiol.* 1994;32:292–300. Other reference viruses used included N119, L6KL5, M184V/Y181C$_{EU}$, M184V$_{pitt}$, HIV-1$_{RTMC}$/MT-2, and HIV-1$_{RTMDR1}$/MT-2, representing nevirapine-resistant Y181C (N119), K103N (L6KL5), nevirapine/3TC-resistant (181C/184V), 3TC-resistant (184V), AZT-resistant (67N/70R/215F/219Q), and nevirapine/AZT/ddI-resistant (74V/41L/106A/215Y) HIV-1, respectively as described by Richman et al., *Proc. Natl. Acad. Sci. USA* 1991;88:11241–11245; Larder and Kemp, *Science* 1989;246:1155–1158; Larder et al., *Nature* 1993;365:451–453; Schinazi et al., *Antimicrob. Agents Chemother.* 1993;37:875–881.

Results

Correlation Between Drug Susceptibility Results Derived by Amp-RT Analysis and Culture-based Assays The Amp-RT IC$_{50}$ values for nevirapine in eight HIV-1 reference isolates were compared with the IC$_{50}$ values obtained by a plaque-reduction assay. Table 3, below, illustrates the level of RT inhibition seen by Amp-RT with $5 \times 10^{-8}$ units of input RT activity from each isolate (the equivalent of 500 HIV-1 particles of the VQA reference virus). The two WT isolates (isolates X267-1 and X165-6) had similar IC$_{50}$ in both assays, while isolates carrying mutations associated with nevirapine resistance (K103N, Y181C, G190A, or Y188L mutations) showed high level of phenotypic resistance (>100-fold increase in IC$_{50}$ compared to WT isolates). A strong correlation ($r^2=0.95$, $p<0.001$) between IC$_{50}$ values determined by Amp-RT and by culture was observed, suggesting that RT-based drug susceptibility testing can be used to determine the HIV-1 phenotype for nevirapine.

TABLE 3

Specificity of Amp-RT Assay versus Culture

| | | IC$_{50}$ ($\mu$M)/fold* | |
|---|---|---|---|
| HIV-1 isolate | Mutations | Culture | Amp-RT |
| X267-1 | — | 0.04 | 4 |
| X165-6 | — | 0.07/1.7 | 11/2.7 |
| X82-5 | K103N, Y181C | 4.6/115 | 491/123 |
| X403-4 | Y181C | 9/225 | 571/143 |
| W786-6 | K103N, Y181C | 20/400 | 2283/570 |
| X165-11 | G190A, Y181C | 22/550 | 1474/369 |
| S469-2/M3 | Y188L | 100/2500 | 2642/661 |
| V818-5 | G190A, Y181C | >100/>2500 | 9804/2451 |

*fold-resistance compared to isolate X267-1

Figure 6:
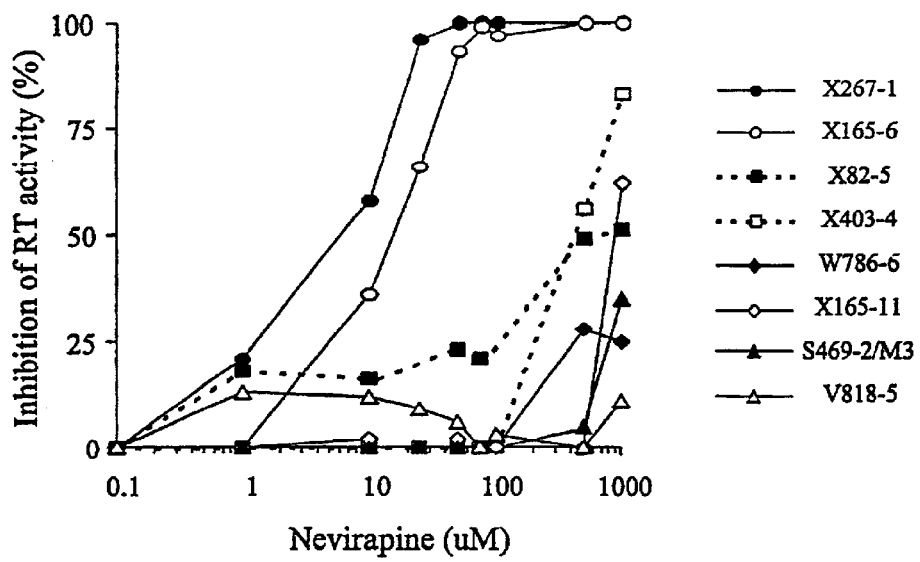
FIG. 6 is a graph of nevirapine concentration versus inhibition of reverse transcriptase activity for wild type and nevirapine-resistant reference isolates.

Detection of Nevirapine Resistance in a Single Amp-RT Reaction Containing 50 $\mu$M Nevirapine The analysis of the RT inhibition values by nevirapine in the wild type and nevirapine-resistant reference isolates demonstrated that a concentration of 50 $\mu$M nevirapine only inhibited the RT from the two wild type isolates (isolates X267-1 and X165-6), while little or no inhibition of RT activity was seen with the resistant isolates as shown in FIG. 6. These results suggest that a single Amp-RT reaction containing 50 $\mu$M nevirapine could be used for rapid screening of nevirapine resistance in plasma.

A concentration of 50 $\mu$M nevirapine was analyzed to determine whether this concentration could distinguish between wild type and nevirapine-resistant HIV-1 RT tested at different levels of input RT activity. As shown in Table 4, below, 50 $\mu$M nevirapine resulted in complete inhibition of approximately $7 \times 10^{-8}$ and $7 \times 10^{-9}$ units of RT activity from a nevirapine-sensitive HIV-1 isolate (isolate X267-1), which are equivalent to approximately 700 and 70 HIV-1 particles of the VQA reference virus, respectively. With a higher input of RT activity ($7 \times 10^{-7}$ units), these conditions resulted in 98.6% RT inhibition. In contrast, no significant inhibition was seen in the nevirapine-resistant HIV-1 RT from isolates X403-4 and W786-6 tested at either high or low input of RT. For example, when $8.3 \times 10^{-9}$ units of RT activity from isolate W786-6 were tested (the equivalent to 80 particles of the VQA reference virus), no significant inhibition by 50 $\mu$M nevirapine was observed as shown in Table 4. These results demonstrate the ability of this assay to distinguish between wild type and nevirapine-resistant RTs within a three-log$_{10}$ range of input RT.

TABLE 4

Effect of Input of RT Activity on RT Inhibition by 50 $\mu$M Nevirapine in the Amp-RT Assay

| | Units of RT activity* | | |
|---|---|---|---|
| HIV-1 isolate | Without Nevirapine | With 50 $\mu$M Nevirapine | Inhibition of RT (%) |
| X267-1 | $7.1 \times 10^{-7}$ | $9.1 \times 10^{-9}$ | 98.7 |
| | $7.2 \times 10^{-8}$ | N.D. | 100 |
| | $6.9 \times 10^{-9}$ | N.D. | 100 |
| X403-4 | $4.4 \times 10^{-7}$ | $3.7 \times 10^{-7}$ | 16 |
| | $8.2 \times 10^{-9}$ | $8.4 \times 10^{-9}$ | 0 |
| | $4.1 \times 10^{-7}$ | $5.0 \times 10^{-7}$ | 0 |
| W786-6 | $5.6 \times 10^{-8}$ | $7.7 \times 10^{-8}$ | 0 |

TABLE 4-continued

Effect of Input of RT Activity on RT Inhibition
by 50 μM Nevirapine in the Amp-RT Assay

| HIV-1 isolate | Units of RT activity* | | Inhibition of RT (%) |
|---|---|---|---|
| | Without Nevirapine | With 50 μM Nevirapine | |

N.D. = not detected
*Mean RT activity observed in at least three different experiments performed in duplicate The specificity of the AMP-RT assay was analyzed to determined whether Amp-RT testing in the presence of 50 μM nevirapine only detected resistance in RTs carrying mutations associated with resistance to nevirapine, and not in RTs carrying other unrelated resistance mutations. Table 5, below, shows that RTs carrying the Y181C and K103N mutations (N119 and L6KL5, respectively) were highly resistant to nevirapine (inhibition values of 0% and 7%). In contrast, viruses containing mutations associated with AZT or 3TC resistance were all found to be susceptible to nevirapine. RT activity from a virus carrying the V106A mutation (HIV-1$_{RTMDR1}$/MT-2) was partially inhibited with 50 μM nevirapine, demonstrating a lower level of resistance to nevirapine compared to RT with the Y181C mutation. Based on these results, Amp-RT conditions containing 50 μM nevirapine were used as a primary screening assay for nevirapine resistance in all subsequent testing of plasma samples unless otherwise indicated.

TABLE 5

Inhibition by 50 μM Nevirapine of Amp-RT Activity
from AZT-, 3TC-, ddI-, and Nevirapine-Resistant HIV-1
Reference Viruses

| Reference virus | Mutations | Phenotype | Inhibition of RT by Nevirapine |
|---|---|---|---|
| HIV-1$_{RTMC}$/MT-2 | 67N/70R/215F/219Q | AZT-resistant | 91.8% |
| M184V$_{pitt}$ | 184V | 3TC-resistant | 98.8% |
| HIV-1$_{RTMDR1}$/MT-2 | 74V/41L/106A/215Y | AZT-, ddI-, nevirapine-resistant | 43% |
| L6KL5 | 103N/75I/77L/116Y/151M | 3TC-, ddI-, ddC-, nevirapine-resistant | 0 |
| M184V/Y181C$_{EU}$ | 184V/181C | 3TC/nevirapine-resistant | 0 |
| N119 | 181C | nevirapine-resistant | 7% |

Figure 7:
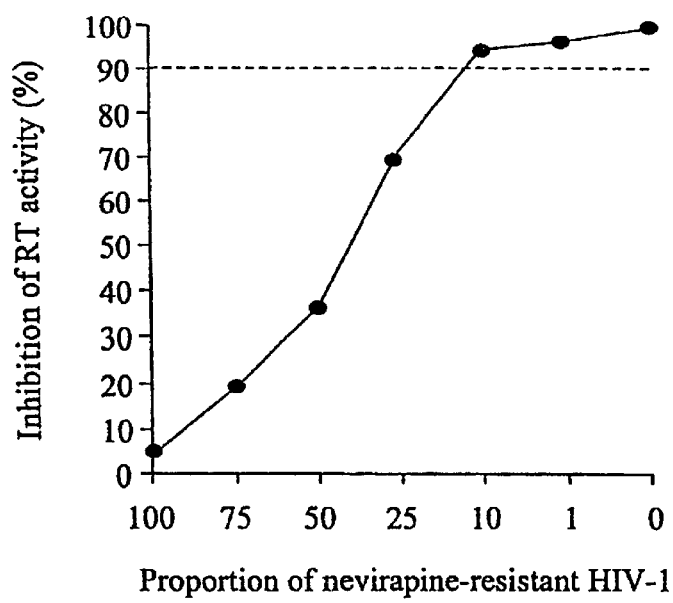
FIG. 7 is a graph of proportion of nevirapine-resistant HIV-1 versus inhibition of reverse transcriptase activity showing an analysis of mixtures of wild type and nevirapine-resistant HIV-1 by the Amp-RT assay described herein.

Detection Threshold of Resistant Virus in Mixtures of Wild Type and Nevirapine-resistant Viruses To determine the detection threshold of the assay, a sensitive (X267-1) HIV-1 clinical isolate and a nevirapine-resistant (W786-6) HIV-1 clinical isolate were mixed at different proportions and tested for evidence of resistance. Both isolates were adjusted to similar levels of RT activity before virus mixtures were prepared. As shown in FIG. 7, values of RT inhibition of >99% were only observed when the sensitive isolate was tested. In contrast, mixtures containing 10% of resistant viruses and 90% of sensitive viruses had RT inhibition values of 94%, suggesting that only sensitive RTs were inhibited by nevirapine and indicating an assay detection threshold for resistant viruses of ~10%. The observed level of RT inhibition in the virus mixtures decreased as the ratio of resistant-to-sensitive viruses increased. For instance, mixtures containing 25% or 75% of resistant viruses had levels of RT inhibition of 80% and 29%, respectively.

Analysis of Phenotypic Resistance to Nevirapine in Plasma and Correlation with Mutations at Codon 181

To validate the assay for detection of phenotypic resistance to nevirapine in HIV-1 from plasma, 30 plasma specimens collected from four patients before and during nevirapine monotherapy (patients N12, N06, N07, and E01) were tested. Phenotypic resistance determined by Amp-RT was compared with the relative proportion of mutations at codon 181 in HIV-1 from plasma (MUT/GNR ratio).

Figure 8:
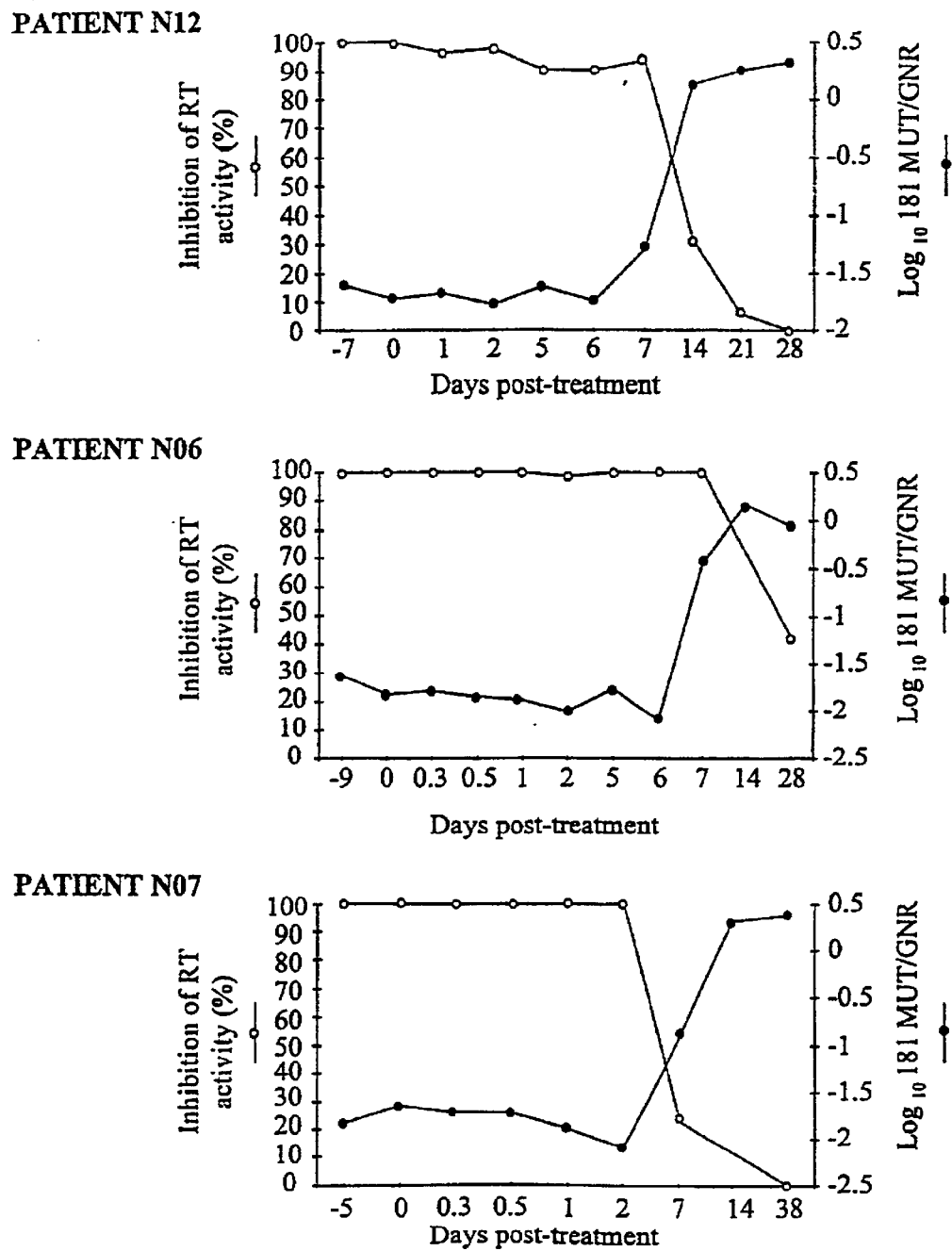
FIG. 8 is a series of three graphs showing days post-treatment with nevirapine versus inhibition of reverse transcriptase activity for three HIV-1-infected patients.

FIG. 8 illustrates the kinetics of detection of both Y181C mutation and evidence of phenotypic resistance to nevirapine in the Amp-RT assay as indicated by decreased level of inhibition of RT in three patients. Patient E01 had only 2 plasma samples taken before and after 28 days of treatment and is not included in the figure. The results show a clear correlation between the decrease in the levels of RT inhibition and the emergence of viruses carrying the Y181C mutation. All samples collected before therapy (n=7) or during the first six days of treatment (n=14) were found to be sensitive to nevirapine, with mean RT inhibition values of 99.3% (range=100%–99.5%) and 98.2% (range=100%–90.4%), respectively. The MUT/GNR ratio in these samples ranged from 0.01 to 0.03 (mean=0.02) before therapy and from 0.008 to 0.02 (mean=0.02) during the first six days of treatment, indicating the absence of detectable Y181C mutation in these samples. The first evidence of phenotypic resistance to nevirapine was found in two samples collected at days 7 and 14 of treatment (patients N07 and N12; RT inhibition values of 24% and 32%, respectively). The observed phenotypic resistance to nevirapine correlated with the detection of the Y181C mutation (MUT/GNR ratio of 0.12 and 1.34, respectively). From two other samples collected after 7 days of treatment, one (patient N12) had borderline susceptibility to nevirapine (RT inhibition of 94%) and a level of Y181C mutation (MUT/GNR ratio of 0.05) at the detection threshold of the genotypic assay (defined as a MUT/GNR ratio of 0.03). The other sample (patient N06) had evidence of detectable Y181C mutation (MUT/GNR ratio of 0.4) and WT susceptibility to nevirapine (RT inhibition value of 100%). The discordant results observed in this particular sample from patient N06 is unexpected because other samples with MUT/GNR ratios of 0.4 and 0.12 had detectable phenotypic resistance by the Amp-RT assay. Phenotypic testing by other methods may be necessary to clarify nevirapine susceptibility in this particular sample.

All samples obtained after more than two weeks of treatment had high levels of phenotypic resistance to nevirapine, with a mean RT inhibition value of 13.82% (range=0%–43. 1%) and mean MUT/GNR ratio of 1.45 (range=0.4–2.16). These results indicate a clear correlation between detection of phenotypic resistance to nevirapine by the Amp-RT assay and emergence of the Y181C mutation and suggest that the assay may be used as a rapid tool for clinical monitoring of phenotypic resistance to nevirapine in HIV-1 from plasma.

Amp-RT IC$_{50}$ Values for Nevirapine in Plasma HIV-1

To quantitate the level of nevirapine resistance, the Amp-RT IC$_{50}$ values in longitudinal samples from patient N12 by testing the plasma RT in the presence of several concentrations of nevirapine were determined. The Amp-RT IC$_{50}$ values observed at days 6 and 7 of therapy (approximately 15 μM) were similar to those observed in WT isolates, indicating WT susceptibility to nevirapine. In contrast, no inhibition was observed in two samples collected at days 21 and 28 of treatment at all concentrations of nevirapine used, resulting in an Amp-RT $IC_{50}$>100 uM. The observed increase in Amp-RT $IC_{50}$ values correlated with the genotypic detection of the Y181C mutation (MUT/GNR ratio of 0.018 and 0.05 at 6 and 7 days, respectively, compared to 1.81 and 2.16 at 21 and 28 days, respectively). These results further validated the use of 50 μM nevirapine in Amp-RT reactions for rapid screening of phenotypic resistance to this drug.

Figure 9:
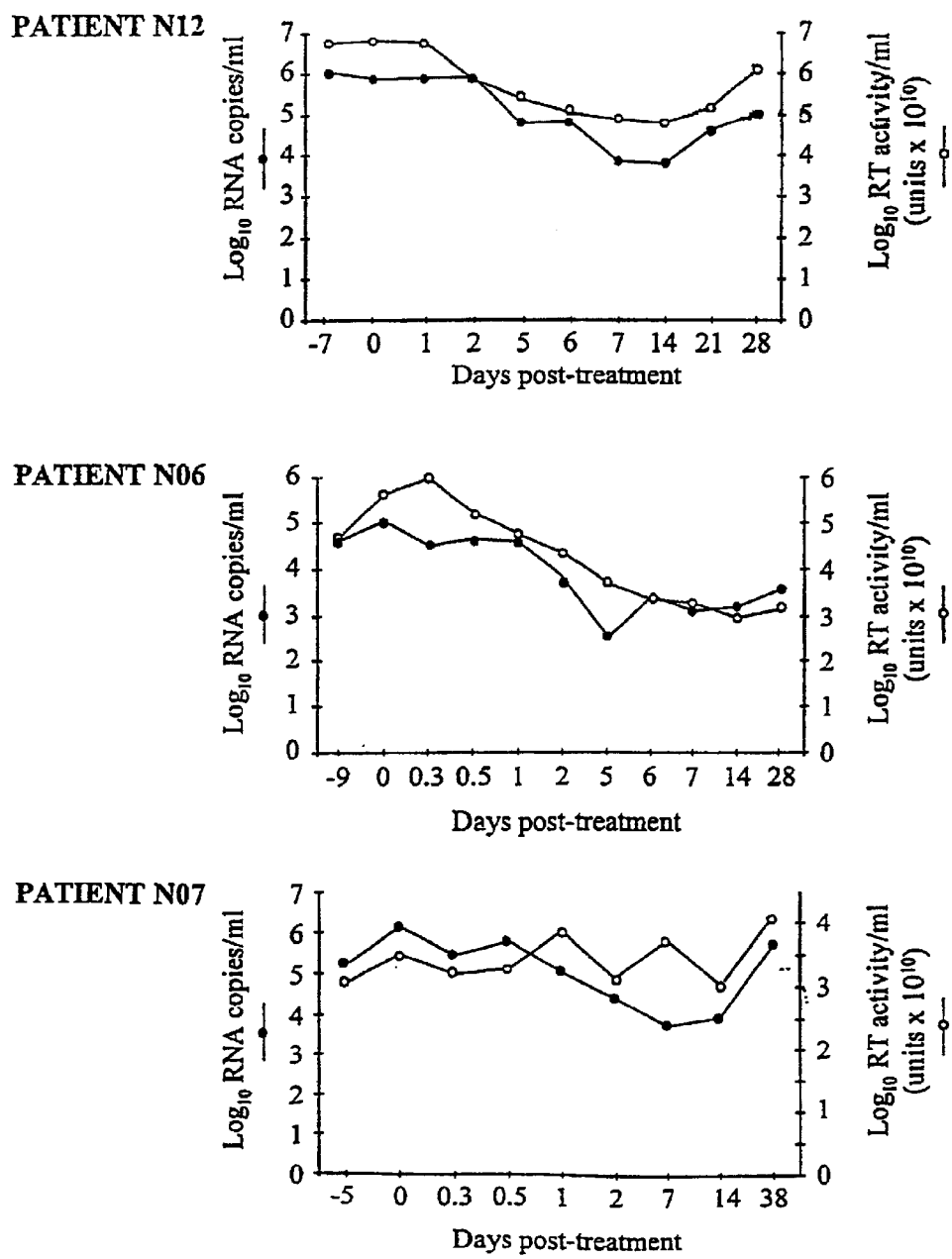
FIG. 9 is a series of three graphs showing days post-treatment with nevriapine versus $\log_{10}$ RNA copies/ml for three HIV-1-infected patients.

Quantitation of Plasma RT Activity by the Amp-RT Assay and Correlation with HIV-1 RNA Levels The kinetics of RT-based viral loads were analyzed and compared with the RNA viral load determined by RT-PCR. FIG. 9 shows levels of both RNA and RT in plasma samples from the three patients who had more than two viral load determinations (patients N12, N06, and N07). RT-based viral loads were derived from Amp-RT reactions made with no nevirapine. The results demonstrated that plasma viral loads measured by RT or RNA were similar for each of the three patients, indicating that the Amp-RT assay may also be used to monitor changes in viral load following antiretroviral therapy.

Conclusions

The Amp-RT assay has several advantages compared to conventional culture-based assays. First, because results are obtained in 1–2 days, the assay provides rapid information on resistance that may assist clinicians in treatment decisions. Second, the assay measures directly phenotypic resistance in HIV-1 from plasma samples, and therefore, does not have selection bias associated with virus isolation in culture.

Phenotypic testing conventionally measures nevirapine susceptibility by analysis of inhibition by several drug concentrations and by determining $IC_{50}$ values. The Amp-RT testing strategy relies on the use of a single drug concentration (50 μM) for rapid screening of nevirapine resistance in plasma. Several observations validate this testing approach. First, complete inhibition of wild type HIV-1 RTs was achieved in Amp-RT reactions containing 50 μM nevirapine. Second, lack of inhibition was only observed in RTs carrying nevirapine-resistance mutations, including Y151C, V106A, K103N, Y190A, G190A, and Y188L. Third, results were reproducible within a wide range of RT levels. Fourth, RT susceptibility results correlated with levels of genotypic markers of resistance (Y181C mutation) in plasma samples. All these findings indicate that analysis of RT inhibition using 50 μM nevirapine in the Amp-RT assay can be used to rapidly screen for nevirapine resistance. However, this testing approach does not provide $IC_{50}$ values for nevirapine. Additional Amp-RT testing with several concentrations of nevirapine is required for quantitating the level of resistance, as shown in four samples from patient N12.

In addition to phenotypic resistance to nevirapine, the assay provides information on levels of functional RT in plasma. The observed correlation between levels of functional RT activity in plasma and HIV-1 RNA viral loads indicates that the Amp-RT testing is suitable for monitoring viral loads following antiretroviral treatment.

The nonnucleoside HIV-1 RT inhibitors comprise a series of structurally diverse compounds that share a common mechanism of action and bind to a common site of the enzyme. Some of the mutations associated with nevirapine resistance confer cross-resistance among this class of compounds. For instance, recombinant viruses carrying the Y181C mutation are highly resistant to delavirdine and loviride in addition to nevirapine, and the K103N mutation confers cross-resistance to efavirenz, delavirdine, and loviride. The foregoing results, indicating that the assay detects resistance mediated by these mutations, suggest that this approach could be adapted for detection of resistance to other nonnucleoside RT inhibitors, such as efavirenz, proposed for treatment of HIV-1-infected individuals.

All of the publications and references mentioned herein are hereby incorporated by reference.

Modifications and variations of the present assay and kit will be obvious to those skilled in the art from the foregoing detailed description. Such modifications and variations are intended to come within the scope of the appended claims.

What is claimed is:

1. A method for the detection of drug resistance of a retrovirus comprising:

a) incubating a first sample comprising the retrovirus with a first added quantity of a reverse transcriptase inhibitor antiviral drug, an RNA template, and a first complementary DNA primer, wherein the RNA template and first complementary DNA primer are oligonucleotides from a region of the encephalomyocarditis virus genome having no significant secondary stucture and less than 50% G-C content, wherein the RNA template directs the synthesis of a DNA product, and b) incubating a second sample comprising the retrovirus with a second added quantity of a reverse transcriptase inhibitor antiviral drug, an RNA template, and a first complementary DNA primer, wherein the RNA template and first complementary DNA primer are oligonucleotides from a region of the encephalomyocarditis virus genome having no significant secondary structure and less than 50% G-C content, wherein the second added quantity of the reverse transcriptase inhibitor drug is measurably less than the first quantity of drug used in a) and wherein the RNA template directs the synthesis of a DNA product; and c) detecting the DNA product produced in a) and b), wherein the quantity of DNA produced in a) relative to the quantity of DNA produced in b) is not reduced, thereby detecting drug resistance or the retrovirus.

2. The method of claim 1, wherein the second quantity of b) is zero.

3. The method of claim 1 wherein the RNA template is an oligonucleotide having the sequence set forth in SEQ ID NO:4.

4. The method of claim 1 wherein the first complementary DNA primer is an oligonucleotide having the sequence set forth in SEQ ID NO:2.

5. The method of claim 1 wherein the reverse transcriptase inhibitor is selected from the group consisting of lamivudine, zalcitabine, didanosine, stavudine, zidovudine, nevirapine, abacavir, delavirdine, loviride, and efavirenz.

6. The method of claim 1 wherein the DNA product is detected by hybridization to a detectable hybridization probe, wherein the hybridization probe is an oligonucleotide having the sequence set forth in SEQ ID NO:3.

7. The method of claim 1 further comprising incubating the retrovirus, RNA template and first complementary DNA primer with a second complementary DNA primer from the encephalomyocarditis virus genome, wherein the second complementary DNA primer amplifies the DNA product.

8. The method of claim 7 wherein the second complementary DNA primer is an oligonucleotide having the sequence set forth in SEQ ID NO:1.

* * * * *

SEQUENCE LISTING

<160> NUMBER OF SEQ ID NOS: 4

<210> SEQ ID NO 1
<211> LENGTH: 20
<212> TYPE: DNA
<213> ORGANISM: Human Immunodeficiency Virus

<400> SEQUENCE: 1
cattagccat ttcaacccat                    20

<210> SEQ ID NO 2
<211> LENGTH: 24
<212> TYPE: DNA
<213> ORGANISM: Human Immunodeficiency Virus

<400> SEQUENCE: 2
gttcatgaca ggccgataca gagg               24

<210> SEQ ID NO 3
<211> LENGTH: 25
<212> TYPE: DNA

<213> ORGANISM: Human Immunodeficiency Virus

<400> SEQUENCE: 3
tgctctcacc ttatcaaaat ccaat                                    25

<210> SEQ ID NO 4
<211> LENGTH: 374
<212> TYPE: DNA
<213> ORGANISM: Human Immunodeficiency Virus

<400> SEQUENCE: 4
cauuagccau uucaacccau gcguuugagg agaagcgcuu ucugauaacc ggugucucc    60 caucagguug ugcagcgacc ucaaugcuaa acacuauaau gaauaauaua auaauuaggg  120
cggguuugua ucucacguau aaaaauuuug aauuugauga ugugaaggug uugucguacg  180
gagaugaucu ccuuguggcc acaaauuacc aauuggauuu ugauaaggug agagcaagcc  240
ucgcaaagac aggauauaag auaacucccg cuaacacaac uucuaccuuu ccucuuaauu  300
cgacgcuuga agacguuguc uucuuaaaaa gaaaguuuaa gaaagagggc ccucuguauc  360
ggccugucau gaac                                                    374